US006953550B2

(12) United States Patent
Sheppard, Jr. et al.

(10) Patent No.: US 6,953,550 B2
(45) Date of Patent: *Oct. 11, 2005

(54) AFFINITY BINDING-BASED SYSTEM FOR DETECTING PARTICULATES IN A FLUID

(75) Inventors: Norman F. Sheppard, Jr., Bedford, MA (US); Alec Mian, Cambridge, MA (US); Gregory Kellogg, Somerville, MA (US); Stephen G. Kieffer-Higgins, Dorchester, MA (US); Bruce L. Carvalho, Watertown, MA (US)

(73) Assignee: Tecan Trading AG, Baar (CH)

( * ) Notice: Subject to any disclaimer, the term of this patent is extended or adjusted under 35 U.S.C. 154(b) by 0 days.

This patent is subject to a terminal disclaimer.

(21) Appl. No.: 10/726,337

(22) Filed: Nov. 30, 2003

(65) Prior Publication Data

US 2004/0142494 A1 Jul. 22, 2004

Related U.S. Application Data

(62) Division of application No. 09/989,259, filed on Nov. 20, 2001, now Pat. No. 6,656,430, which is a division of application No. 09/614,834, filed on Jul. 20, 2000, now Pat. No. 6,319,468, which is a division of application No. 08/995,056, filed on Dec. 19, 1997, now Pat. No. 6,143,247.
(60) Provisional application No. 60/034,327, filed on Dec. 20, 1996.

(51) Int. Cl.$^7$ .............................................. G01N 21/00
(52) U.S. Cl. .................. 422/63; 422/64; 422/68.1; 422/50; 422/72; 422/101; 422/102; 422/67; 436/45; 436/63; 436/177; 436/180; 210/787; 210/380.1; 210/374; 210/780; 210/109; 210/781; 435/7.1; 435/7.2; 435/7.21
(58) Field of Search .................. 432/63, 64, 68.1, 432/50, 72, 101, 102, 67; 436/45, 63, 177, 180; 210/787, 380.1, 374, 780, 109, 781; 435/7.1, 7.2, 7.21

(56) References Cited

U.S. PATENT DOCUMENTS

| | | | |
|---|---|---|---|
| 3,615,222 A | 10/1971 | Mead | |
| 3,743,482 A | 7/1973 | Eisentraut | |
| 4,546,460 A | 10/1985 | Ando | |
| 5,009,997 A | 4/1991 | Shah et al. | |
| 5,091,318 A | 2/1992 | Anawis et al. | |
| 5,137,031 A | 8/1992 | Guirguis | |

(Continued)

FOREIGN PATENT DOCUMENTS

| | | |
|---|---|---|
| EP | 0 634 654 A2 | 4/1994 |
| WO | WO 92/07243 A1 | 4/1992 |
| WO | WO 93/22053 A1 | 11/1993 |
| WO | WO 94/16543 A1 | 7/1994 |

OTHER PUBLICATIONS

Cozens–Roberts et al., "Receptor–mediated adhesion phenomena" *Biophys. J* . 58:107–125 (Jul. 1990).
Prime et al., "Adsorption of Proteins onto Surfaces Containing End–Attached Oligo (ethylene oxide): A Model System Using Self–Assembled Monolayers" *J. Am. Chem. Soc.* 115:10714–21 (1993).
Singhvi et al., "Engineering Cell Shape and Function" *Science* 264:696–698 (Apr. 29, 1994).

(Continued)

*Primary Examiner*—Christopher L. Chin
*Assistant Examiner*—Pensee T. Do
(74) *Attorney, Agent, or Firm*—McDonnell Boehnen Hulbert & Berghoff

(57) ABSTRACT

This invention provides methods and apparatus for detecting and quantifying particulate matter suspended in a fluid. Specifically, the invention provides an integrated, affinity-binding based, analytical system comprising a platform for performing an affinity-binding based assay for specifically binding particulates including microbial cells, and a detection means for detecting the particulates specifically bound to a defined surface or chamber comprising the platform. Methods for using the analytical systems of the invention are also provided.

4 Claims, 30 Drawing Sheets

U.S. PATENT DOCUMENTS

| | | | |
|---|---|---|---|
| 5,229,297 A | * 7/1993 | Schnipelsky et al. | ......... 435/94 |
| 5,278,048 A | 1/1994 | Parce et al. | |
| 5,296,375 A | 3/1994 | Kricka et al. | |
| 5,304,487 A | 4/1994 | Wilding et al. | |
| 5,338,689 A | 8/1994 | Yves et al. | |
| 5,399,486 A | * 3/1995 | Cathey et al. | ............... 435/7.9 |
| 5,403,720 A | 4/1995 | Sato et al. | |
| 5,427,946 A | 6/1995 | Kricka et al. | |
| 5,451,504 A | 9/1995 | Fitzpatrick et al. | |
| 5,460,940 A | 10/1995 | Yves et al. | |
| 5,460,979 A | 10/1995 | Levine et al. | |
| 5,491,067 A | 2/1996 | Setcavage et al. | |
| 5,496,697 A | 3/1996 | Parce et al. | |
| 5,506,141 A | 4/1996 | Weinreb et al. | |
| 5,512,432 A | 4/1996 | Lapierre et al. | |
| 5,547,849 A | 8/1996 | Baer et al. | |
| 5,556,764 A | 9/1996 | Sizto et al. | |
| 5,637,469 A | 6/1997 | Wilding et al. | |
| 5,672,861 A | 9/1997 | Fairley et al. | |
| 6,143,247 A | * 11/2000 | Sheppard et al. | ............. 422/63 |
| 6,319,468 B1 | * 11/2001 | Sheppard et al. | ............. 422/63 |
| 6,319,469 B1 | * 11/2001 | Mian et al. | ................... 422/64 |

OTHER PUBLICATIONS

Owicki et al., "Biosensors based on the energy metabolism of living cells: The physical chemistry and cell biology of extracellular acidification" *Biosensors & Bioelectronics* 7:255–272 (1992).

Raymond Dessy "Waveguides as Chemical Sensors" *Analytical Chemistry* 61(19)1079A–1094A (Oct. 1, 1989).

Nakagawa et al., "A Micro Chemical Analyzing System Integrated on a Silicon Wafer" *Proc. IEEE* 89–95 (1990).

Rosenzweig et al., "Laser–Based Particle–Counting Microimmunoassay for the Analysis of Single Human Erythrocytes" *Anal. Chem.* 66:1771–1776 (1994).

Haab et al. "Single Molecule Fluorescence Burst of Detection of DNA Fragments Separated by Capillary Electrophoresis" Anal. Chem. 67:3253–3260 (1995).

* cited by examiner cross-section AA'

AFFINITY BINDING-BASED SYSTEM FOR DETECTING PARTICULATES IN A FLUID

This application is a divisional of U.S. Ser. No. 09/989,259, filed Nov. 20, 2001, now U.S. Pat. No. 6,656,430, issued Dec. 2, 2003, which is a divisional of U.S. Ser. No. 09/614,834, filed Jul. 20, 2000, now U.S. Pat. No. 6,319,468, issued Nov. 20, 2001, which is a divisional application of U.S. Ser. No. 08/995,056, filed Dec. 19, 1997, now U.S. Pat. No. 6,143,247, issued Nov. 7, 2000, which claims priority to U.S. Provisional Application Ser. No. 60/034,327, filed Dec. 20, 1996.

BACKGROUND OF THE INVENTION

1. Field of the Invention

This invention relates to methods and apparatus for detecting, characterizing and quantifying particulate matter suspended in a fluid. More specifically, the invention provides an integrated, affinity-binding based analytical system for detecting particulates, particularly cells, suspended in a fluid, especially a biological fluid. In particular, the invention provides a platform for performing an affinity-binding based assay for specifically binding particulates including cells, and a detection means for detecting the particulates specifically bound to a defined surface or chamber comprising the platform. In addition, the invention provides such analytical systems to facilitate cell accumulation in a specific cell accumulation area or chamber of the platform, allowing particulate counting and characterization using the platform, as well as high throughput screening of test compounds to determine the capacity of the compound to affect cell viability, metabolism or physiology. Devices for manipulating the platforms of the invention are provided comprising detection means operatively arranged relative to the platform, as well as devices that provide detecting means for manually-manipulated platforms. Methods for using the platforms of the invention are also provided.

2. Background of the Related Art

Determining the type, concentration and properties of particulates in a fluid is important in a variety of contexts. Dust and dirt particles in water, oil or other industrial fluids can negatively impact on the performance and useful lifetime of complex machinery. Pyrogens, including bacterial cells, in pharmaceutical products, or manufacturing facilities making such products, can compromise the safety and reliability of available drugs. Similarly, cells, particularly bacterial cells, that are themselves disease-causing (such as *Salmonella* spp.) or that make toxins (such as botulism toxin) are hazardous, and advantageously are screened in manufacturing and other settings where foodstuffs or other consumables are produced. Finally, mammalian cells, including sperm cells and hematopoietic cells, are usefully analyzed in the corresponding biological fluids for diagnostic and treatment monitoring purposes.

Certain methods and apparatus for detecting biological molecules and cells are known in the prior art.

U.S. Pat. No. 3,615,222 issued Oct. 26, 1971 to Mead discloses a specific binding method for detecting a component of a biological fluid.

U.S. Pat. No. 3,743,482 issued Jul. 3, 1973 to Eisentraut discloses a method for determining thyroid function U.S. Pat. No. 3,907,502 issued Sep. 23, 1975 to Brink discloses a method for identifying Bence Jones proteins.

U.S. Pat. No. 4,546,460 issued Oct. 8, 1985 to Ando discloses a videodisc autofocus device.

U.S. Pat. No. 5,009,997 issued Apr. 23, 1991 to Shah et al. discloses two-site immunometric sandwich assay.

U.S. Pat. No. 5,091,318 issued Feb. 25, 1992 to Anawis et al. discloses binding of allergens to a solid phase.

International Application, Publication No. WO92/07243, published on Apr. 30, 1992 in the name of Cellpro, disclose the use of a biological particle separator.

U.S. Pat. No. 5,137,031 issued Aug. 11, 1992 to Guirguis discloses a urine testing apparatus and cell collection.

U.S. Pat. No. 5,278,048 issued Jan. 11, 1994 to Parce et al. discloses an apparatus for detecting the effect of a test compound on a living cell.

U.S. Pat. No. 5,296,375, issued Mar. 22, 1994 to Kricka et al. disclose microplatforms for detecting the presence of an analyte in a fluid.

U.S. Pat. No. 5,304,487, issued Apr. 19, 1994 to Kricka et al disclose microplatforms for detecting the presence of an analyte in a fluid.

International Application, Publication No. WO94/16543, published on Jul. 21, 1994 in the name of Schutze et al., disclose the use of a laser optical trap for manipulating living cells.

U.S. Pat. No. 5,338,689 issued Aug. 16, 1994 to Yves et al. discloses a method for detecting antigens and antibodies.

U.S. Pat. No. 5,403,720 issued Apr. 4, 1995 to Sato et al. discloses a method for detecting microorganisms.

U.S. Pat. No. 5,427,946, issued Jun. 27, 1995 to Kricka et al. disclose microplatforms for detecting the presence of an analyte in a fluid.

U.S. Pat. No. 5,451,504 issued Sep. 19, 1995 to Fitzpatrick et al. discloses a membrane strip for detecting the presence of an analyte in a sample.

European Application, Publication No. EP634654, published on Oct. 4, 1995 in the name of Ventura disclose an apparatus for measuring purified water quality.

U.S. Pat. No. 5,460,940 issued Oct. 24, 1995 to Yves et al. discloses a method for detecting antigens and antibodies.

U.S. Pat. No. 5,460,979 issued Oct. 24, 1995 to Levine et al. discloses an indirect fluorescent assay of blood samples.

U.S. Pat. No. 5,491,067 issued Feb. 13, 1996 to Setcavage et al. discloses an agglutination reaction and separation vessel.

U.S. Pat. No. 5,496,697 issued Mar. 5, 1996 to Parce et al. disclose an apparatus for detecting the effect of test compounds on cells.

U.S. Pat. No. 5,498,392, issued Mar. 12, 1996 to Kricka et al. disclose microplatforms for detecting the presence of an analyte in a fluid.

U.S. Pat. No. 5,506,141 issued Apr. 9, 1996 to Weinreb et al. discloses an apertured cell carrier.

U.S. Pat. No. 5,512,432 issued Apr. 30, 1996 to Lapierre et al. discloses methods for detecting antigens and antibodies.

U.S. Pat. No. 5,547,849 issued Aug. 20, 1996 to Baer et al. discloses an apparatus and method for volumetric capillary cytometry.

U.S. Pat. No. 5,556,764 issued Sep. 17, 1996 to Sizto et al. discloses an apparatus and method for cell counting and classification.

International Application, Publication No. WO96/12962, published on May 2, 1996 in the name of Biocircuits Corp. disclose detection of an analyte using particles and a specific binding pair in the presence of a transparent surface.

U.S. Pat. No. 5,637,469, issued Jun. 10, 1996 to Kricka et al. disclose microplatforms for detecting the presence of an analyte in a fluid.

U.S. Pat. No. 5,672,861 issued Sep. 30, 1997 to Fairley et al. discloses an automatic focusing device for a confocal laser microscope.

However, despite this cited prior art there remains a need in the art for methods and apparatus to detect particulates in fluids, particularly cells in biological fluids, rapidly, simply, reliably and more economically than available using the prior art.

SUMMARY OF THE INVENTION

This invention provides an integrated, affinity-binding based, analytical apparatus for detecting particulates, particularly cells, suspended in a fluid, preferably a biological fluid. The invention provides a platform for performing an affinity-binding based assay for specifically binding particulates such as cells, preferably microbial cells, especially bacterial cells, and mammalian cells, especially hematopoietic cells, and a detection means for detecting the particulates specifically bound to a defined surface or chamber comprising the platform. Methods for using the platforms of the invention are also provided.

In one aspect of the invention is provided an affinity-binding based, analytical apparatus for detecting particulates suspended in a fluid. The apparatus provided by the invention comprises a platform having a surface defining a detection chamber, whereby a specific binding reagent is deposited on the surface of the chamber and specifically binds the particulate to be detected. In preferred embodiments, the specific binding reagent is an antibody, a ligand, a lectin, an integrin, an antigen, a receptor, a carbohydrate or an adhesion molecule. Preferably, the surface of the detection chamber is also treated with a blocking compound that discourages non-specific binding to the surface of the chamber. In another preferred embodiment, the platform is a rotatable structure, most preferably a disk. In a preferred embodiment of this aspect of the invention, the disk is a microplatform as disclosed in co-owned and co-pending Ser. No. 08/768,990, filed Dec. 18, 1996, incorporated by reference. The platforms of the invention also preferably comprise fluid sample input means, overflow reservoirs, wash buffer reservoirs, and fluid waste receptacles, in fluid connection with each other as described herein, as well as air displacement vents or orifices, or means for removing the fluid component of a sample applied thereto.

Means for detecting specifically-bound particles in the surface or chamber are also provided. Preferred embodiments of detecting means are a light source, particularly a monochromatic light source, and a detector therefor. In addition, preferred embodiments of the platforms of the invention comprise reservoirs containing detectable labeling reagents and moieties for detecting particulates retained on the detection chambers of the platforms. In preferred embodiments, said reagents and moieties comprise stains, preferably histochemical stains and most preferably vital stains, that specifically bind to the particulates, most preferably cells, in the detection chambers of the platforms of the invention. In additional preferred embodiments, said reagents and moieties comprise immunochemical reagents, preferably antisera and antibodies and most preferably monoclonal antibodies, that specifically bind to the particulates, most preferably cells, in the detection chambers of the platforms of the invention. In preferred embodiments, said antisera and antibodies are labeled with a detectable label. Preferred detectable labels include fluorescent labels and enzymatic moieties capable of converting a substrate to a detectable product. In alternative preferred embodiments, the detectable reagents comprise a first antisera or antibody specific for the particulate to be detected, most preferably a cell, and a second antisera or antibody that specifically recognizes and binds to said first antisera or antibody, and is itself detectably labeled. Preferred detectors include photodetectors, most preferably photodiodes, avalanche photodiodes, photocells and photomultiplier tubes.

In a second embodiment of this aspect of the invention is provided an apparatus that comprises a platform having a surface defining a cell accumulation chamber, whereby particulates that are cells, preferably microbial cells, especially bacterial cells, and mammalian cells, especially hematopoietic cells, accumulate in the chamber and are detected therein. Preferably, in certain embodiments, the chamber also comprises a filtering means having a pore size that prevents the cells from leaving the chamber when the fluid comprising the sample is replaced by buffer solutions, detection reagents or other fluid volumes. In other embodiments, the chamber preferably comprises a non-specific cell adhesion coating on the surface thereof that retains the cells in the chamber. In another preferred embodiments, the surface is treated to permit the cells to attach and multiply in the cell accumulation chamber of the platforms of the invention.

In additional preferred embodiments, the platform is a rotatable structure, most preferably a disk. In a preferred embodiment of this aspect of the invention, the disk is a microplatform as disclosed in co-owned and co-pending Ser. No. 08/768,990, filed Dec. 18, 1996, incorporated by reference. The platforms of the invention also preferably comprise fluid sample input means, overflow reservoirs, wash buffer reservoirs, fluid waste receptacles, or reservoirs containing an amount of a detectable labeling moiety for labeling the cells retained in the accumulation chamber, in fluid communication with each other as described herein, or air displacement vents or orifices, or means for removing the fluid component of a sample applied thereto.

In alternative embodiments, the platforms of the invention are provided to detect, quantitate and characterize the effect(s) of a test compound on a cell, most preferably on the metabolism, physiology or viability of the cell. In such embodiments, platforms are provided with reservoirs containing a test compound and other components therefor. In such embodiments, cells retained in the cell accumulation chamber of a platform of the invention are treated with a test compound contained in a reservoir in fluid communication with the cell accumulation chamber. Said test compound is transferred to the cell accumulation chamber, most preferably replacing the fluid sample, for a time and under conditions wherein the test compound can have an effect on the cell. Alternatively, the test compound can comprise a component of the cell accumulation chamber as provided. Detection of cell viability, for example using vital stains, or cellular physiology or metabolism by detecting metabolites or other cell products produced in response to the test compound is achieved using the platforms of the invention, wherein reagents for detecting said effect-associated molecules produced by the cells are introduced into the cell accumulation chamber prior to detection. In these embodiments, detection of the effect-associated molecules is achieved using reagents specific for said molecules and detection means specific for said reagents. Most preferably, the effect-associated molecules are detected using photodetectable reagents such as dyes, most preferably fluorescent dyes, which are contained in a reservoir in fluid communication with the cell accumulation chamber and delivered thereto after treatment of the cells with the test compound.

Means for detecting specifically-bound particles in the surface or chamber are also provided. Preferred embodiments of detecting means are a light source, particularly a monochromatic light source, and a detector therefor. In addition, preferred embodiments of the platforms of the invention comprise reservoirs containing detectable labeling reagents and moieties for detecting particulates retained on the cell accumulation chambers of the platforms. In preferred embodiments, said reagents and moieties comprise stains, preferably histochemical stains and most preferably vital stains, that specifically bind to the particulates, most preferably cells, in the cell accumulation chambers of the platforms of the invention. In additional preferred embodiments, said reagents and moieties comprise immunochemical reagents, preferably antisera and antibodies and most preferably monoclonal antibodies, that specifically bind to the particulates, most preferably cells, in the cell accumulation chambers of the platforms of the invention. In preferred embodiments, said antisera and antibodies are labeled with a detectable label. Preferred detectable labels include fluorescent labels and enzymatic moieties capable of converting a substrate to a detectable product. In alternative preferred embodiments, the detectable reagents comprise a first antisera or antibody specific for the particulate to be detected, most preferably a cell, and a second antisera or antibody that specifically recognizes and binds to said first antisera or antibody, and is itself detectably labeled. Preferred detectors include photodetectors, most preferably photodiodes, avalanche photodiodes, photocells and photomultiplier tubes.

Additional embodiments of each of these aspects of the invention include platforms comprising a multiplicity of the components of the cell detection arrays of the invention as defined herein, thereby providing for the analysis of multiple aliquots of the same sample or multiple samples on the same platform.

In a second aspect of the invention, an affinity-binding based, analytical apparatus is provided that is a combination of two elements. The first element is a platform as described herein. In preferred embodiments of these aspects of the invention, the platform is a rotatable platform having a means for being rotated about a central axis comprising a rotational element, preferably a hole for a spindle. In these aspects of the invention various components of the platform are connected to one another by channels, most preferably microchannels as defined herein. The second element in this aspect of the invention is a device comprising a holding means for accommodating the platforms of the invention, most preferably also including detecting means for detecting particulates and most preferably cells on the platforms of the invention. In preferred embodiments, the devices of the invention are provided as a device that comprises rotating means and controlling means thereof, and components of a detecting means operably positioned to detect binding of particulates on the platform surface and most preferably in a detection or cell accumulation chamber of the platform. In these aspects of the invention, fluid displacement through the components of the platforms of the invention is motivated by centripetal force produced by rotation of the platform about the central axis at a speed and for a time determined by controlling means comprising the device. In a preferred embodiment, the platform and device comprise a disk and player/reader device as disclosed in co-owned and co-pending U.S. Ser. No. 08/768,990, filed Dec. 18, 1996 and incorporated by reference.

Methods for analyzing a fluid, preferably a biological fluid, to detect particulates suspended therein using the platforms of the invention are also provided. In preferred embodiments, the methods provided by the invention comprise the steps of, first, applying a fluid sample to the surface of the platform, preferably to a fluid sample input means, and most preferably wherein said means further comprises means for metering a specific volume of the fluid into a detection or cell accumulation chamber on the surface of the platform.

In certain embodiments of the methods of the invention a metered amount of the fluid sample applied to the platform is transferred to a detection or cell accumulation-chamber. For the purposes of this invention, the term "a metered amount" will be understood to mean a volumetric amount of the fluid sample that fills a metering means in the fluid sample input means, wherein volumetric amounts greater than the metered amount are removed from the fluid sample input means into an overflow chamber or fluid waste receptacle. In preferred embodiments, the metered amount of the fluid sample provided on an inventive platform is from about 10 $\mu$L to about 500 $\mu$L.

In certain embodiments of the methods of the invention the amount of the fluid sample applied to the platform is transferred to a detection chamber coated with a specific binding reagent and incubated thereupon for a time and under conditions wherein specific binding is achieved between the particulates comprising the fluid sample and the specific binding reagent, thereby immobilizing the particulate in the detection chamber, and removing the fluid sample from the chamber. In preferred embodiments, the cells in the detection chamber are washed with a solution, preferably a buffer and more preferably a buffer comprising a component, preferably a salt or detergent, that dissociates particulates retained in the chamber by non-specific binding unrelated to binding of the particulate to the specific binding reagent and does not dissociate binding of the particulate to the specific binding reagent; said washing solution is preferably removed from the chamber prior to cell detection to effect removal of non-specifically retained particulates. The selective removal of non-specifically bound particulates is accomplished by precisely controlling the surface shear force exerted on the particulates by the fluid flowing through the detection chamber. Thereafter the presence, identity and number of particulates in the detection chamber are detected. In certain embodiments of the methods of the invention, a solution containing a reagent for detecting a particulate in the detection chamber is added to the chamber before detection of the particulate is accomplished, most preferably by contacting the cells retained in the detection chamber with such reagents. In certain embodiments of this aspect of the methods of the invention, particulates, preferably cells are stained with a specific dye either prior to application to the platform or after the particulates are retained in the detection chamber. In additional preferred embodiments, the reagent is an antisera or antibody, most preferably a monoclonal antibody, linked to a detectable marker such as a fluorescent compound. In other preferred embodiments, the reagent is an antisera or antibody, most preferably a monoclonal antibody, linked to an enzyme capable of converting a substrate to a detectable product; in such embodiments, the appropriate substrate is also added to the particulates prior to application to the platform or more preferably after the particulates are retained in the detection chamber, in a concentration, for a time and under conditions whereby the substrate is converted to the detectable product. In preferred embodiments, the particulates detected in fluid samples using the methods of the invention are cells, preferably microbial cells, especially bacterial cells, and mammalian cells, most preferably hematopoietic cells.

In other embodiments of the methods of the invention, the metered amount of the fluid sample applied to the platform is transferred to a cell accumulation chamber that retains the cells therein upon evacuation of the chamber of the fluid sample or replacement of the fluid sample with other fluid components of the platforms of the invention. In these embodiments, the fluid sample is incubated in the cell accumulation chamber for a time and under conditions wherein cells are retained in the chamber, after which the fluid sample is removed from the chamber. In preferred embodiments, the cells in the cell accumulation chamber are washed with a solution, preferably a buffer and more preferably a buffer comprising a component, preferably a salt or detergent, that dissociates non-cellular particulates from the chamber but does not remove the cells from the chamber; said washing solution is preferably removed from the chamber prior to cell detection to effect removal of non-cellular particulates. Thereafter the presence, identity and number of cells in the accumulation chamber are detected.

In alternative embodiments, the effect of a test compound on a cell, most preferably on the metabolism, physiology or viability of the cell, is determined using the methods of the invention. In such embodiments, cells retained in the cell accumulation chamber of a platform of the invention are treated with a test compound for a time and under conditions wherein the test compound can have an effect on the cell. Detection of cell viability, for example using vital stains, or cellular physiology or metabolism by detecting metabolites or other cell products is achieved using the platforms of the invention, wherein reagents for detecting said effect-associated molecules produced by the cells are introduced into the cell accumulation chamber prior to detection. In these embodiments, detection of the effect-associated molecules is achieved using reagents specific for said molecules and detection means specific for said reagents. Most preferably, the effect-associated molecules are detected using photodetectable reagents such as dyes, most preferably fluorescent dyes.

In certain embodiments of the methods of the invention, a solution containing a reagent for detecting a particulate in the cell accumulation chamber is added to the chamber before detection of the particulate is accomplished, most preferably by contacting the cells retained in the chamber with such reagents. In certain embodiments of this aspect of the methods of the invention, particulates, preferably cells are stained with a specific dye either prior to application to the platform or after the particulates are retained in the cell accumulation chamber. In additional preferred embodiments, the reagent is an antisera or antibody, most preferably a monoclonal antibody, linked to a detectable marker such as a fluorescent compound. In other preferred embodiments, the reagent is an antisera or antibody, most preferably a monoclonal antibody, linked to an enzyme capable of converting a substrate to a detectable product; in such embodiments, the appropriate substrate is also added to the particulates prior to application to the platform or more preferably after the particulates are retained in the cell accumulation chamber, in a concentration, for a time and under conditions whereby the substrate is converted to the detectable product. In preferred embodiments, the particulates detected in fluid samples using the methods of the invention are cells, preferably microbial cells, especially bacterial cells, and mammalian cells, most preferably hematopoietic cells.

Certain preferred embodiments of the apparatus of the invention are described in greater detail in the following sections of this application and in the drawings.

BRIEF DESCRIPTION OF THE DRAWINGS

FIG. 1 is a schematic illustration of affinity-based platforms of the invention.

FIG. 3 contains illustrations of arrangements of platform components useful for enumerating particulates in a fluid, for example cell counting.

FIG. 4 contains illustrations of arrangements of platform components useful for studying the effect of a test molecule or molecules on populations of cells for enumerating particulates in a fluid, for example cell counting.

FIG. 6 illustrates means and methods for counting and studying individual cells using platforms of the type FIG. 1C. In FIG. 6B track widths 72 are modulated such that reflections from the two side lobes 73 produce a modulated signal. Amplitude or frequency modulation, achieved by varying the geometry of the tracks 75, can be used to encode positional information. FIG. 6C illustrates another arrangement where information is encoded by the presence or absence of reflective features in the central track.

DETAILED DESCRIPTION OF PREFERRED EMBODIMENTS

Figure 1A:
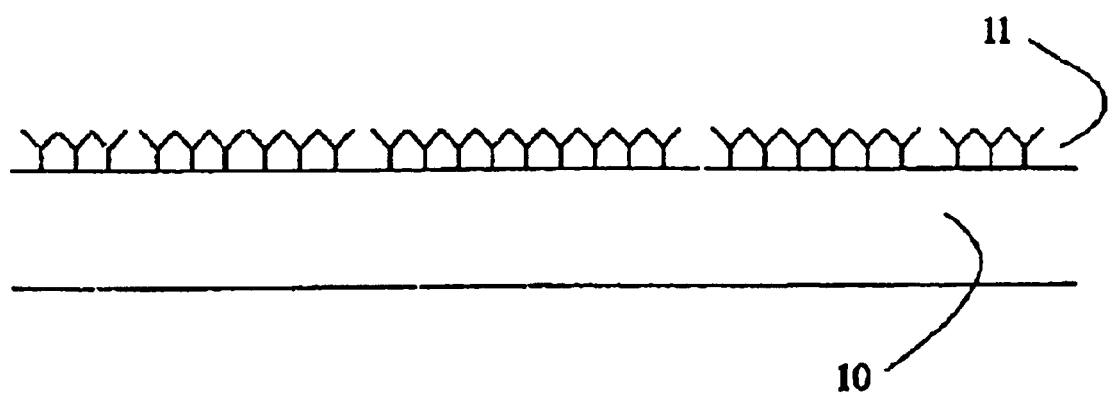
FIG. 1A is comprised of a substrate 10 coated with a specific binding reagent comprising a first member of an affinity binding pair 11.

This invention provides a platform for performing analytical assays of fluid samples, preferably biological fluid samples. For the purposes of this invention, the term "sample" will be understood to encompass any fluid containing a particulate species of interest, wherein the particulate species is preferably a cell and more preferably microbial cells or somatic cells and most preferably bacterial cells and hematopoietic cells.

For the purposes of this invention, the term "platform" is intended to encompass any solid support structure providing a surface or comprising a chamber that can be treated to comprise a specific binding reagent. Preferably, the platforms of the invention are rotatable about a central axis, providing for movement of sample and other reagents on the platform under the influence of centripetal force. More preferred embodiments of the platforms of the invention are circular disks that are rotatable about a central aperture adaptably shaped to accommodate a spindle or other rotating means. Most preferred embodiments of the platforms of the invention are platforms as disclosed in U.S. patent application Ser. No. 08/68,990, filed Dec. 18, 1996 and incorporated by reference, and in U.S. Provisional Application Ser. No. 60/034,327, filed Dec. 20, 1996, the disclosures of each of which are explicitly incorporated by reference herein.

In one aspect of the platforms of the invention is provided a surface or detection chamber treated to comprise a specific binding reagent. For the purposes of this invention, the term "specific binding reagent" is intended to encompass biomolecules having a specific binding affinity between pairs thereof providing a specific molecular binding interaction with a binding affinity constant of between about $10^{-4}$ and $10^{-15}$ M. Examples of such pairs of specific binding reagents include but are not limited to antigen and antibody, including antisera, polyclonal antibodies and most preferably monoclonal antibodies; receptor and ligands, including cell-surface receptors; integrins and adhesion proteins, including ICAM-I and ICAM-II; and carbohydrates and lectins, including phytohemagglutinin. As provided by the invention, specific binding reagents comprising a first member of a specific binding pair is provided coating a surface or detection chamber of a platform designed or intended to detect the presence of a particulate, most preferably a cell expressing a cognate antigen, receptor or adhesion protein or having a carbohydrate moiety at the cell surface specific for a particular lectin. Said specific binding reagent is applied to the surface or detection chamber of the platform by depositing the reagent on the surface using any appropriate means, including inkjet printing, computer-positioned syringes, microetching and microlithographic methods, including photolithography, screen and airbrush printing methods, solution coating, dipping, and conventional microtitre-well techniques. In applying said specific binding reagent, the surface or detection chamber can be treated to provide a two-dimensional array or pattern, wherein certain areas on the surface or detection chamber are treated with said specific binding reagent and others are not in a recognizable manner. In preferred embodiments, a surface or detection chamber of the invention is provided having transparent portions coated with a specific binding reagent, and other portions coated with a reflective material to provide a reflecting surface in a pattern alternating with the transparent, coated portions. In alternative embodiments, a multiplicity of specific binding reagents of distinct specificity are applied to a surface or detection chamber of the platform, or each of a multiplicity of specific binding reagents of distinct specificity are applied to different areas or regions of a surface or detection chamber of a platform of the invention, thereby providing a pattern of such distinct specific binding reagents on the platform. Such arrays can be discrete arrays each comprising a different specific binding reagent or can be integrated to comprise a pattern of each of the multiplicity of distinct specific binding reagents. Exemplary patterns include alternating strips, checks, and concentric circles. Similarly, patterns of transparent, specific binding reagent-coated portions and reflective, non-binding portions are provided by the invention. Exemplary patterns include alternating strips, checks, and concentric circles, most preferably comprising a pattern resembling or comprising a "bar code." In addition, the portions of the surface of the platform not treated with said specific binding reagent, and most preferably portions of the surface of the platform comprising reflective portions are advantageously treated with a blocking agent, such as bovine serum albumin (BSA) to prevent non-specific binding of particulate matter on the surface of the platform.

Preferred patterns of reflective and specific binding portions of the surfaces of the platforms of the invention are provided analogous to and as a specific modification of technology developed in the prior art for optical information storage (e.g. CD-ROM applications). This technology is based on detecting the presence or absence of signal features having dimensions on the order of 1 micron embedded in a plastic substrate. The detectors or "optical heads" incorporate servomechanisms designed to automatically position a focal point of light in both a direction normal to the disk and laterally in the plane of the disk to submicron accuracy. The focusing, tracking and data acquisition functions of the optical head are implemented using a diode-laser, optical elements (diffraction gratings, lenses (including cylindrical lenses), mirrors, polarizers) and multiple detectors. The light emitted from the laser is split into-multiple beams (typically 2 or 3) and directed on to the disk. The light reflected from each of the beams is coupled back into the optical head where it is directed to a number of photodiodes (typically 6). The outputs from the photodiodes are combined in various ways (either added or subtracted) to obtain both the data and signals for controlling the tracking and focusing. Tracking, or following the data stream, is accomplished by moving the optical head in a radial direction, while simultaneously controlling the rate of rotation of the disk. The radial positioning is derived from the light reflected from the regions of the disk on either side of the data pits.

This approach has been modified for detection of particles or cells. The platform of FIG. 1D is advantageously provided as an optical disk wherein digital information has been encoded in an standard format; however, in the platforms of the invention, the thickness of the substrate is thinned sufficiently so that the presence of particles on the surface will interfere with the reading of the encoded data using the optical detection system pictured in FIG. 5E. A second variation uses the optically transparent substrate is provided having parallel tracks defined by alternating transparent and reflective regions or surfaces, as is pictured in FIGS. 1C, 6B and 6C. This is done, for example, using established microlithographic methods to selectively etch vacuum-deposited gold from a glass or quartz substrate. In one embodiment of the platforms of the invention, a pair of reflective stripes and intervening transparent region are provided to form a "track". The transparent region contains "data" in the form of the presence or absence of cells; this "data" is provided in the practice of the methods of the invention upon specific particulate binding to the transparent region, while the reflective regions provides a means for accomplishing the tracking and focusing. To confine the cells to the transparent region, it is advantageous to place the cells on the side of the substrate on which the reflective material has been deposited. The presence of two chemically different surfaces permits selective chemical modification of the transparent and reflective surfaces that promotes (i.e. in the transparent region) or prevents (i.e. in the reflective region) adhesion of the cells to be detected.

An optical head similar, in principle, to that used for optical information storage is used as provided by the methods of the invention to interrogate the plane to which the cells are adhered through the transparent substrate. The optical head uses a light source (e.g. a diode laser operating at 650 nm) and optical elements to focus multiple beams of light on or in the plane of the platform adherent to cells or particles. The secondary or sub-beams are used for tracking and focusing, while the primary or main beam illuminates the transparent region comprising the particles or cells. The presence or absence of a cell in the track is detected by a number of means, for example by modulating the transmission of light through the disk to an opposing detector, or by fluorescent emission. For example, in the case of fluorescence, the light emitted light may be detected by a detector (typically a photomultiplier tube (PMT)) and appropriate filter positioned either directly opposite the light source, at an oblique angle to the platform and/or the light source, or as part of an optical head which has been designed to collect light emitted back from disk (i.e. at an angle of about 0 degrees).

The platforms of the invention advantageously comprise additional fluid-handling components attached to the surface or detection chamber or cell accumulation chamber on the platforms. These components can be fabricated as described below either integral to the disk or as modules attached to, placed upon, in contact with or embedded in the disk. Such components are preferably provided in combinations of related components as described in further detail herein that are in fluid communication. For the purposes of this invention, the term "in fluid communication" or "fluidly connected" is intended to define components that are operably interconnected to allow fluid flow between components. In preferred embodiments, the platform comprises a rotatable platform, more preferably a disk, whereby fluid movement on the disk is motivated by centripetal force upon rotation of the disk.

The platforms of the invention further comprise a sample entry port, preferably comprising metering elements to deliver a volumetric amount of sample fluid to the detection or cell accumulation chamber of the platform. In these embodiments, the platforms of the invention are also provided with an overflow reservoir for retaining excess fluid applied to the platform in excess of the amount metered into the detection or cell accumulation chamber, most preferably in fluid communication with the fluid sample input means wherein excess fluid is transferred to the overflow reservoir by capillary action. The metering sample port is designed to rapidly wick in fluid presented to the opening. The overflow chamber is connected to the entry port to take off any excess fluid not wicked into the capillary bed. The volume of the sample is thereby defined by the number and cross section of the capillaries.

Additional chambers on the platform contain fluids such as a wash buffer and staining solution. The fluid components are in fluid communication via narrow bore capillaries of defined cross section, which form capillary valves. Fluid in the chambers and components of the platforms of the invention will be retained until sufficient driving force overcomes the surface tension of the fluid. Differing cross sections allow fluids to be moved independently by controlling the force applied (e.g. by controlling rotation rate).

In embodiments of the apparatus of the invention comprising the inventive platforms, the invention also comprises a device for manipulating the disks of the invention, wherein the disk is rotated within the device to provide centripetal force to effect fluid flow on the disk. Accordingly, the device provides means for rotating the disk at a controlled rotational velocity, for stopping and starting disk rotation, and advantageously for changing the direction of rotation of the disk. Both electromechanical means and control means, as further described herein, are provided as components of the devices of the invention. User interface means (such as a keypad and a display) are also provided.

In such embodiments, fluid (including reagents, samples and other liquid components) movement is controlled by centripetal acceleration due to rotation of the platform, and by the selective activation of valves controlling the communications between the components of the systems comprising the platform. The magnitude of centripetal acceleration required for fluid to flow at a rate and under a pressure appropriate for a particular system is determined by factors including but not limited to the effective radius of the platform, the position angle of the structures on the platform with respect to the direction of rotation and the speed of rotation of the platform.

In other embodiments, fluid flow is provided on the platforms of the invention by mechanical means, including but not limited to pumping using the creation of air or liquid pressure between the components of the platform to effect fluid movement, using pumping means sufficient to achieve fluid movement. These means might include syringe pumps or HPLC pumps. In certain other embodiments of the platforms of the invention, fluid movement is motivated by rapid manual displacement of the platform followed by a sharp stop of such displacement; this might be actuated by a spring mechanism or simply a "flick of the wrist".

It has been shown (Cozens-Roberts et al., 1990, *Biophys. J.* 58: 107–125) that cells and particles coated with one member of a binding pair have a relatively well-defined value of surface shear, called the critical shear rate, $S_c$, at which the will detach from a surface to which they are bound. This value is determined by the number and strength of bonds to the surface, as well as the size of the cell in question. The removal of non-specifically (adventitiously) bound particles or cells is effected by precisely controlling shear rates at value less than $S_c$.

Advantageous components of the platforms of the invention include fluid sample input means, including volumetric metering means, channels for fluid flow between components, reagent reservoirs, mixing chambers, optical reading chambers, and most preferably incubation surfaces or detection chambers comprising a specific binding reagent deposited thereupon, and cell accumulation chambers comprising non-specific cell adhesion compounds, filtering means that retain cells in the chamber or treated surfaces that permit the cells to attach thereto. Also advantageously comprising certain embodiments of the inventive platforms are valves for controlling fluid flow between components, temperature control elements, separation channels, air outlet ports, sample outlet ports, mixing means including magnetic, acoustic and preferably mechanical mixers, liquid and dry reagents, and other components as described herein or known to the skilled artisan.

Sample is applied to the detection or cell accumulation chamber of the platforms of the invention either directly or more preferably by transfer of a metered amount of a portion of the sample from a fluid sample input means to the chamber, for example, by the selective opening of valves controlling access to the chamber from the fluid sample input means. Said valves include but are not limited to microvalves as described in more detail below including mechanical, electrical and thermal valve mechanisms, as well as capillary microvalves wherein fluid flow is controlled by the relationship between capillary forces and centripetal forces acting on the fluid. Reagent reservoirs, wash buffer reservoirs, other fluidic components and the contents thereof are connected to one another and to the detection and cell accumulation chamber through channels, preferably microchannels as defined herein, controlled by such valves. In preferred embodiments, delivery of fluids through such channels is achieved by the coincident rotation of the platform for a time and at a rotational velocity sufficient to motivate fluid movement between the desired components, and opening of the appropriate valves. The amount of a fluid, or a reagent comprising a fluid, delivered to the detection or cell accumulation chamber is thus controlled by the speed of rotation and the time during which the valve to the reagent reservoirs is open.

Figure 5A:
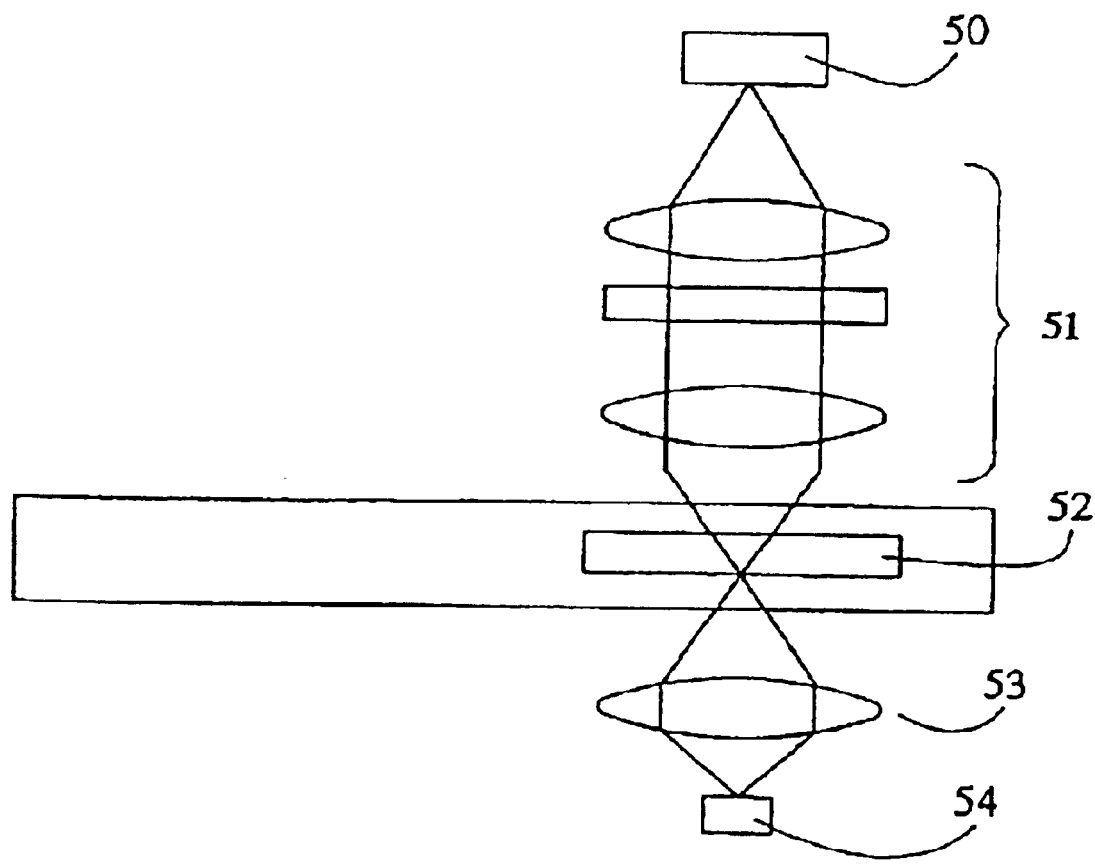
FIG. 5 contains schematic illustrations of optical detection systems suitable for detecting the presence and/or optical properties of particulates bound to the platforms of the invention. The apparatus of FIG. 5A, suitable for transmission, light scattering or direct fluorescence measurement of a platform such as illustrated in FIG. 1A, comprises a light source 54, focusing lens system 53, assembly 51 comprising optical elements to collect, filter and focus light onto the photodetector 50.
FIG. 5B incorporates the detection elements of FIG. 5A, and would be suitable for chemiluminescence or bioluminescence measurements.
FIG. 5C is a rearrangement of the components of FIG. 5A for use where the light is reflected from platforms of the type shown in FIG. 1B.
FIG. 5D is an apparatus suitable for fluorescence detection on platforms 1A and 1C, where the assembly of optical elements 55 includes elements such as excitation and emission filters, a dichroic mirror and lenses.
FIG. 5E is an apparatus suited for use with platforms 1D. The elements 56 comprise those necessary to read data from an optical disc such as a CD-ROM.
Figure 5B:
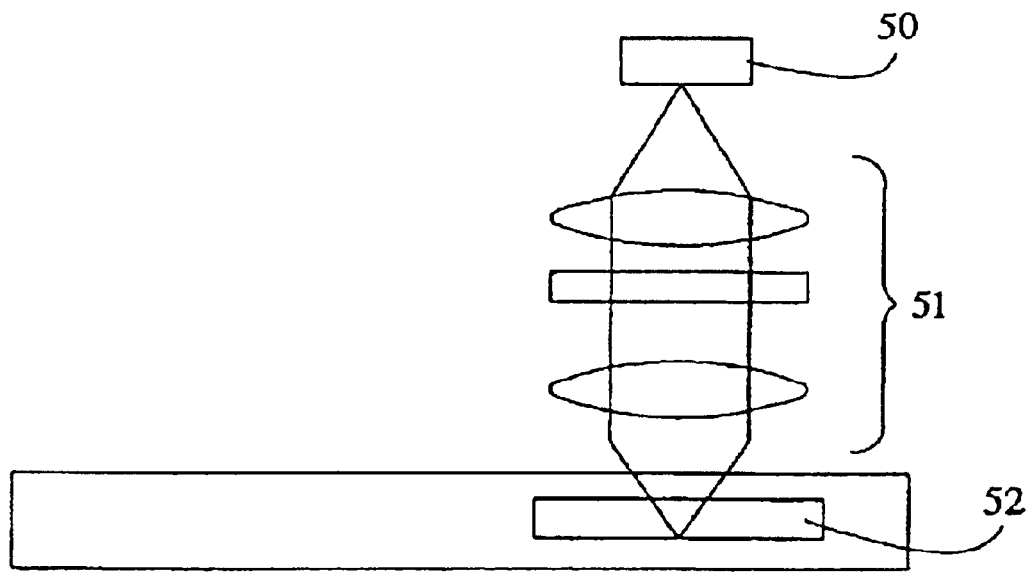
Figure 5C:
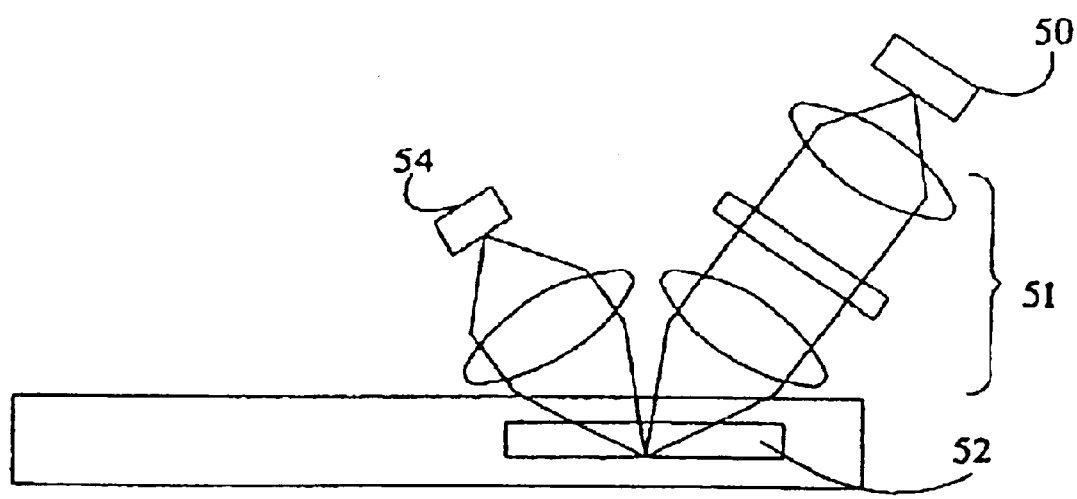
Figure 5D:
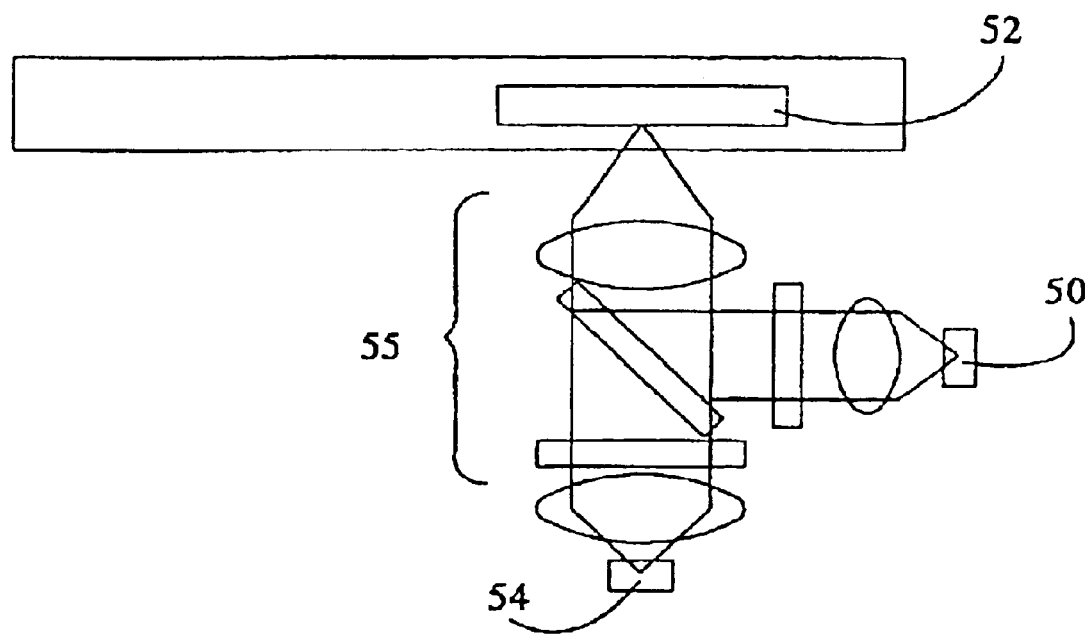
Figure 5E:
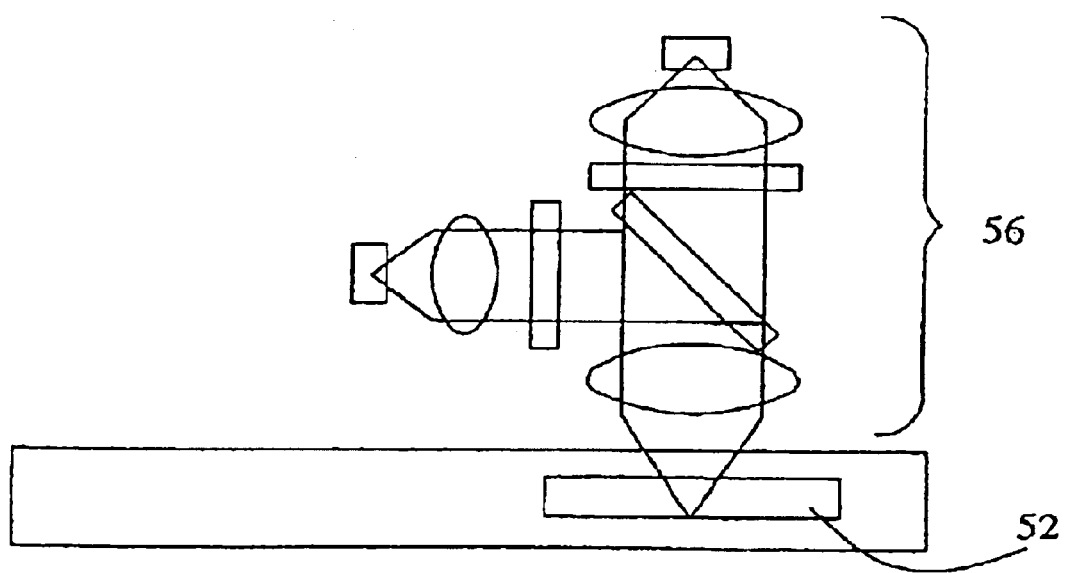

The apparatus of the invention also provides detection systems for detecting, monitoring, quantitating or analyzing particulates specifically retained on the surface of the platform, in a detection chamber comprising a specific binding reagent or in a cell accumulation chamber as described herein. Detection systems useful in the manufacture and use of the platforms of the invention include, but are not limited to, fluorescent, chemiluminescent, colorimetric, or scattering measurements. FIG. 5 illustrates optical systems for effecting these measurements. The apparatus of FIG. 5A, suitable for transmission, light scattering or direct fluorescence measurement of a platform such as illustrated in FIG. 1A, comprises a light source 54, focusing lens system 53, assembly 51 comprising optical elements to collect, filter and focus light onto the photodetector 50. FIG. 5B incorporates the detection elements of FIG. 5A, and would be suitable for chemiluminescence or bioluminescence measurements. FIG. 5C is a rearrangement of the components of FIG. 5A for use where the light is reflected from platforms of the type shown in FIG. 1B. FIG. 5D is an apparatus suitable for fluorescence detection on platforms shown in FIGS. 1A and 1C, where the assembly of optical elements 55 includes elements such as excitation and emission filters, a dichroic mirror and lenses. FIG. 5E is an apparatus suited for use with platforms shown in FIG. 1D. The elements 56 comprise those necessary to read data from an optical disc such as a CD-ROM, electrochemical and radioactivity detecting means. Optionally, the detection system can be integral to the platform and can comprise a simple visual detection means such as the development of a visible color. Alternatively, the detection system can comprise a component of a device manipulating the platform, preferably comprising an optical detecting means. Also included in the invention are devices comprising a light source for illuminating the platform and a magnifying means to facilitate visual inspection (direct or computer-aided imaging) of the platform. Non-optical detection systems such as electrochemical and radioactivity detecting means may also be used. Embodiments wherein components of the detecting means comprise both the platform and the device are also encompassed by the invention.

In certain applications it may be desirable to increase the surface area available for specific binding by particles in order to increase the capacity for binding particles within a certain area of the device. The use of porous filter or tortuously-connected microchannels which have been treated with one half of the binding pair would provide such a high surface area.

In operation, such a system would be similar to an affinity chromatography column. Fluid containing particles would be flowed through the porous structure. (Pore size must be chosen to avoid clogging by the largest particles present.) In addition to creating a large surface area available for binding, the particles will be forced near the binding surfaces as they flow through the pores, increasing the probability of binding.

An application of such a system would be in detection of cells either through a direct or indirect means. In this application, cells may be mixed with a buffer containing antibody-linked labels such as gold nanoparticles (~100 nm in size or smaller than a cell) or enzyme-linked antibodies. The cells are then flowed through the porous structure, binding via a different binding molecule. In the case of gold sol particles, if a sufficient volume is passed through the filter such that the total number of cells captured is large, a diffuse reflectance measurement can accurately quantitate the amount of gold trapped in the filter. In the case of an enzymatic assay, an appropriate substrate may be flowed into the porous structure and the evolved dye spectrophotometrically measured.

A second application of such a system would be as a cell concentrator. Sample may be flowed into the porous structure and appropriate particles bind to the material. A very large volume of sample may flow thorough the structure, such that eventually the number of trapped particles is many orders of magnitude orders of magnitude greater in concentration that in the fluid.

At this point, direct assays may be performed on the particles trapped in the structure. Another possibility is to flow a buffer through the structure which dissociates the affinity bond between particle and structure. The highly-concentrated particles may then be transported to another reservoir for further processing.

In preferred embodiments, the detection or cell accumulation chamber of the platform of the invention is constructed so that the height (depth) of the chamber is smaller than the other dimensions of the chamber. Preferably, the height (depth) of the chamber ranges from about 25 $\mu$m to 1 mm. Most preferably, the chamber has a volume of from about 5 $\mu$L to about 1000 $\mu$L, more preferably from about 50 $\mu$L to about 500 $\mu$L.

Platform Design, Coatings and Composition

Platforms of the invention such as disks and the components comprising such platforms are advantageously provided having a variety of composition and surface coatings appropriate for a particular application. Platform composition will be a function of structural requirements, manufacturing processes, and reagent compatibility/chemical resistance properties. Specifically, platforms are provided that are made from inorganic crystalline or amorphous materials, e.g. silicon, silica, quartz, inert metals, or from organic materials such as plastics, for example, poly(methyl methacrylate) (PMMA), acetonitrile-butadiene-styrene (ABS), polycarbonate, polyethylene, polystyrene, polyolefins, polypropylene and metallocene. These may be used with unmodified or modified surfaces as described below. Also provided by the invention are platforms made of composites or combinations of these materials, for example, platforms manufactures of a plastic material having embedded therein an optically transparent glass surface comprising for example the detection chamber of the platform.

The surface properties of these materials may be modified for specific applications. For example, appropriate surface-modification can either encourage or suppress cell and/or protein absorption. Surface modification can be achieved by silanization, ion implantation and chemical treatment with inert-gas plasmas (i.e., gases through which electrical currents are passed to create ionization). In preferred embodiments, a particular portion of the surface of the platform, most preferably comprising a chamber in the platform, is treated with a specific binding reagent. In preferred embodiments, the specific binding reagent is a protein (e.g., an antibody, a receptor or adhesion protein), an antigen or a receptor ligand (e.g., a small molecule such as a peptide), or a lectin (such as phytohemagglutinin) or a carbohydrate that is recognized by a lectin. Preferably, the surface is treated with such specific binding reagents to form an insoluble and difficult-to-dissociate bond between the reagent and the surface, to minimize loss of the reagent during subsequent treatment steps (such as washing). The surface is treated with the reagent to saturate the surface with the reagent over a defined portion of the surface. In preferred embodiments, the treatment of the surface with a specific binding reagent constitutes a pattern of deposition on the surface than can be recognized, and most preferably, digitized to provide a two-dimensional map of the surface for orienting a detecting means. Surfaces treated with a multiplicity of specific binding reagents, most preferably in a recognizable pattern of deposition, are within the scope of the invention disclosed herein.

Also provided by the platforms of the invention are surfaces comprising detection and cell accumulation detectors that are porous, i.e. comprising a three-dimensional surface in which specific binding reagents or particulates can be bound.

In advantageous embodiments, the specific binding reagent is deposited on the surface in optically transparent portions thereof in combination with deposition in alternative and adjacent regions of the surface with a reflective material treated to prevent particulate binding thereupon. Reflective material of the appropriate feature size is most advantageously prepared using methods and means developed for the manufacture of microelectronic circuits. In a process known as "lift-off", a negative image of the desired features is produced in a photoresist material using microlithography. A reflective layer comprising one or more metal layers is deposited by evaporation, after which the photoresist and overlying metal is removed (typically by dissolution of the photoresist layer) leaving the desired patterns on the surface of the substrate. Alternatively, the portion of the surface comprising the specific binding reagent is also reflective but is prepared so that this surface can be distinguished from the adjacent reflective surfaces. In these embodiments, the differential patterns of optical transmission and reflection are useful for orienting a light source of a detecting means, particularly a monochromatic and most preferably a coherent or laser light source, over the appropriate portion of the surface of the platform for detecting the particulates retained thereupon. In particularly preferred embodiments, the surface comprises a pattern of reflective coatings that are used to orient, digitize and quantitate the particulates, most preferably cells, contained within a defined area of the platform comprising the detection or cell accumulation chamber.

In embodiments of the inventive platforms wherein the reflective metal layer is gold, the surface can be treated with omega-substituted alkanethiol compounds of general formula —HS—$(CH_2)_n$—R (where n is an integer from 1 to about 50, and R is an alkyl, alkenyl alkynyl, aryl or alkaryl group, or substituted derivatives thereof), to form self-assembled monolayers (SAM). SAMs formed from poly (ethylene glycol) terminated alkane thiols (e.g., R=(CH$_2$CH$_2$O)$_m$CH$_3$) resist protein adhesion (see Prime et al., 1993, *J. Amer. Chem. Soc.* 115: 10714–10721) and have been used to block cell adhesion (see Singhvi et al., 1994, *Science* 264: 696–698). Gold surfaces have been coated with SAMs of hexadecanethiol (n=15, R=—CH$_3$) to which laminin was adsorbed to provide a substrate suitable for cell attachment and growth (Singhvi et al., ibid.).

The surface of the platform, particularly the area defining the detection or cell accumulation chamber, is also advantageously treated with a non-specific blocking agent or agents to prevent non-specific binding of particulates, particularly cells, to the surface of the platform. The nature and extent to which such treatments are necessary depends strongly on the nature of the surface. For example, a strong correlation has been established between water contact angle and cell adsorption, with hydrophilic surfaces showing significantly less cell adsorption than hydrophobic surfaces (see Ikada, 1994, *Biomaterials* 15: 725). Silicon, silica, and quartz present an inherently high-energy, hydrophilic surface. Alteration of surface properties is attained through hydroxylation (achieved, for example, by NaOH treatment at high temperatures) or silanization. Substituted silanes and siloxanes are particularly appropriate for increasing the hydrophilicity of an otherwise hydrophobic surface. These compounds consist of one or several reactive head-groups which bond (chemically or through hydrogen-bonding) to a substrate, for example, a core region of alkane (—CH$_2$O—). These compounds also provide a route for more sophisticated alteration of surface properties (such as derivation with functional groups to obtain the surface properties of interest). A wide variety of such functionalities can be introduced at a surface, including vinyl, phenyl, methylene and methoxy groups, as well as surfaces providing mixed functionalities. These functional groups not only change gross properties like liquid contact angle, but provide sites for preferential adsorption of molecules, either per se or as a result of further conjugation of specific binding reagents such as peptide ligands, antibodies and the like. More preferably, the surface is treated after deposition of the specific binding reagent(s) with a non-specific blocking agent, including but not limited to bovine serum albumin and casein.

Plastic-based platforms and disks can also be readily treated to achieve the required surface properties. Inert-gas or reactive-gas plasmas are used to alter surface energies through the formation of surface complexes, for example, hydroxyl-rich surfaces for increased hydrophilicity, or perfluorinated surfaces for increased hydrophobicity. For example, surface graft polymerization is a technique used to graft polymers or oligomers with the desired surface properties to a substrate polymer chosen for its bulk processability and manufacturing properties, such as a plastic. Commercial methods for initiating graft polymerization include gamma radiation, laser radiation, thermal or mechanical processing, photochemical processes, plasma, and wet chemical processes (further discussed in *Encyclopedia of Polymer Science and Technology*, 2$^{nd}$ ed., (Supplement), Wiley & Sons: New York, 1989, pp 675–689). Chemical modification of polymer surfaces (and appropriate polymers) includes oxidations (polyethylenes), reductions (fluoropolymers), sulfonations, dehydrohalogenations (dehydrofluorination of poly (vinylidene fluoride)) and hydrolyses. While the chemical nature of the surface is altered through chemical modification, mechanical properties, durability and chemical resistance are primarily a function of the substrate plastic. For example, surface grafting of poly(ethylene glycol) (PEG) onto polyethylene yields a surface that is both hydrophilic (unlike polyethylene) and resistant to water (PEG is itself soluble in water, while polyethylene is not). Finally, silanization of organic polymer surfaces can also be performed, providing a wide variety of surface energy/chemistry combinations.

Platform Components

The platforms of the invention are preferably provided with a multiplicity of components, either fabricated directly onto the platform, or placed on the platform as prefabricated modules. In addition to the integral components, certain devices and elements can be located external to the platform, optimally positioned on a device of the invention in relation to the platform, or placed in contact with the platform either while rotating or when at rest. Components optimally comprising the platforms of the invention or a controlling device in combination therewith include detection chambers, reservoirs, valving mechanisms, detectors, sensors, temperature control elements, filters, mixing elements, and control systems.

The invention provides a detection chamber or cell accumulation chamber, or a surface or specialized section of the platform, upon which specific components of a fluid sample, preferably cells and most preferably microbial cells, especially bacterial cells, and mammalian cells, especially hematopoietic cells, can be retained. In certain preferred embodiments, cells are retained in the chamber by interaction with specific binding reagents, including but not limited to ligands, lectins, peptides, proteins, antibodies or fragments thereof derivatized to be retained within the surface of the platform. In other preferred embodiments, cells are retained in an accumulation chamber by non-specific binding to adhesion molecules, or physical retention using filtering or other means as described below, or by allowing the cells to attach to a substrate that has been specifically surface modified to facilitate or promote such attachment. Particulates captured by such specific binding can be eluted from the surface of the platform and transferred to a collection reservoir by treatment with appropriately-chosen ionic strength buffers, using conventional methods developed for immunological or chromatographic techniques. More preferably, particulates, particularly cells and most particularly microbial cells, can be specifically retained in the detection or cell accumulation chamber, surface or specialized section of the platform and detected using detecting means as described herein. In other preferred embodiments, cellular particulates retained in the detection or cell accumulation chamber, or on any surface or specialized section of the platform can be counted, localized on the surface, or characterized using the detecting means of the apparatus of the invention. In preferred embodiments, cells retained in detection or cell accumulation chambers are monitored for viability, metabolism, the effect of viral infection or drugs on viability or metabolism, or used for toxicity screening assays.

In advantageous embodiments, cells are retained in a detection or cell accumulation chamber on a platform of the invention and incubated in the presence of a test compound for a time and under conditions whereby the test compound may have an effect on cell metabolism, physiology or viability. The cells are then detected, and most preferably quantitatively detected, to determine the effect of the test compound on the cell. For example, cytotoxicity testing can be performed on a cell, most preferably a mammalian cell, by incubating the test compound with cells retained in the cell accumulation chamber on the platform, followed by a determination of cell viability using visual, microscopic or spectrophotometric detection of the exclusion from the treated cells of a detectably colored "vital" stain, used according to the understanding in the art. Such determinations can be performed in the presence or absence on the test compound, most preferably in multiplex fashion on the same platform, and a comparison made between the observed cell viability in the presence and absence of the test compound.

In additional embodiments, arrays of specific binding reagents, including but not limited to ligands, lectins, peptides, proteins, antibodies or fragments thereof can be deposited in a detection chamber or on a surface or specialized section of a platform, preferably forming a patterned array that can be detected visually or using the detecting means disclosed herein. Also provided are such arrays that are digitized based on the signal per unit area detected from the array, so that the position of a signal with a detection chamber, or on a surface or specialized section of the platform, indicating a particulate can be identified and specifically tracked during metabolic, viability, toxicity or other assays. The capacity to collect time-integrated information in such assays is also advantageously provided.

The platform may contain reservoirs and chambers for containing fluids, such as the washing buffer used to detach nonspecifically bound particulates from the surface of the detection chamber, or a solution of a compound to which cells in the cell accumulation chamber are going to be exposed. The chambers may be prefilled with liquid components and sealed using valving mechanisms, may be filled with dried reagents which are resolubilized by the addition of a fluid such as water, or may be filled at the time of use with prepared liquid reagents.

The platforms of the invention also are provided comprising reservoirs and chambers for containing fluids, such as the washing buffer used to detach nonspecifically bound particulates from the surface of the detection chamber, or a solution of a compound to which cells in the cell accumulation chamber are to be exposed. The chambers may be prefilled with liquid components and sealed using valving mechanisms, may be filled with dried reagents which are resolubilized by the addition of a fluid such as water, or may be filled at the time of use with prepared liquid reagents.

In certain embodiments, the platforms of the invention also are provided comprising fluid waste receptacles and overflow receptacles and reservoirs for holding excess fluid comprising unmetered sample, wash buffers and sample fluid after displaced from the detection and cell accumulation chambers of the platforms of the invention, or any other source of excess fluid produced in the practice and use of the platforms of the invention. It will be recognized that in some embodiments, such excess fluid will be simply removed from the platforms either by user intervention, or by the placement of an outlet in the platform that permits excess fluid to drain therefrom.

The components of the platforms of the invention are in fluidic contract with one another. In preferred embodiments, fluidic contact is provided by microchannels comprising the surface of the platforms of the invention. Microchannel sizes are optimally determined by specific applications and by the amount of delivery rates required for each particular embodiment of the platforms and methods of the invention. Microchannel sizes can range from 0.1 $\mu$m to a value close to the 1 mm thickness of the platform. Microchannel shapes can be trapezoid, circular or other geometric shapes as required. Microchannels preferably are embedded in a platform having a thickness of about 0.1 to 100 mm, wherein the cross-sectional dimension of the microchannels across the thickness dimension of the platform is less than 500 $\mu$m and from 1 to 90 percent of said cross-sectional dimension of the platform.

Valving mechanisms are provided to control of fluid movement and transfer on the platform. The nature of the valves useful in the platforms of the invention are essentially identical to the valves and microvalves disclosed in co-owned and co-pending U.S. Ser. No. 08/768,990, filed Dec. 18, 1996, explicitly incorporated by reference herein. These valve include mechanical, thermal and capillary valves.

Examples of such microvalves include a piezo activator comprising a glass plate sandwiched between two silicon wafers, as described by Nakagawa et al. (1990, Proc. IEEE Workshop of Micro Electro Mechanical Systems, Napa Valley, Calif. pp. 89); a pneumatically-actuated microvalve, as described by Veider et al. (1995, Eurosensors IX, pp. 284–286, Stockholm, Sweden, June 25–29); a micromachined gas valve (that is commercially available; Redwood Microsystems, Menlo Park, Calif.; ICSensors, Milpitas, Calif.); a pressure-balanced microvalve, as disclosed by Huff et al. (1994, $7^{th}$ International. Conference on Solid-State Sensors and Actuators, pp. 98–101); a polymeric relaxation valve; and a capillary microvalve. In the latter embodiment, which is based on the use of rotationally-induced fluid pressure to overcome capillary forces, it is recognized that fluid flow is dependent on the orientation of the surfaces of the components. Fluids which completely or partially wet the material of the microchannels; reservoirs, detection chambers, etc. (i.e., the components) of the platforms of the invention which contain them experience a resistance to flow when moving from a component of narrow cross-section to one of larger cross-section, while those fluids which do not wet these materials resist flowing from components of the platforms of the invention of large cross-section to those with smaller cross-section. This capillary pressure varies inversely with the sizes of the two components, or combinations thereof, the surface tension of the fluid, and the contact angle of the fluid on the material of the components. Generally, the details of the cross-sectional shape are not important, but the dependence on cross-sectional dimension results in microchannels of dimension less than 500 $\mu$m exhibit significant capillary pressure. By varying the intersection shapes, materials and cross-sectional areas of the components of the platform of the invention, "valves" are fashioned that require the application of a particular pressure on the fluid to induce fluid flow. This pressure is applied in the disks of the invention by rotation of the disk (which has been shown above to vary with the square of the rotational frequency, with the radial position and with the extent of the fluid in the radial direction). By varying capillary valve cross-sectional dimensions as well as the position and extent along the radial direction of the fluid handling components of the platforms of the invention, capillary valves are formed to release fluid flow in a rotation-dependent manner, using rotation rates of from 100 rpm to several thousand rpm. This arrangement allows complex, multistep fluid processes to be carried out using a predetermined, monotonic increase in rotational rate.

Control of the valves of the platforms provided by the invention is achieved either using on-platform controller elements, device-specific controllers, or a combination thereof.

Optical detecting means are also provided as components of the apparatus of the invention. The photodetectors of the invention are optimally provided to detect optical absorbance/transmittance, fluorescence, light-scattering or other optical signals, which are processed and translated into data on the position, number and viability of cells on the platform. Embodiments of such platforms and devices comprising scanning arrays are also provided. Also advantageously provided by the invention are detecting means for tracking and focusing the light source on the surface of the platform, and actuating means for positioning the light source on the surface of the platform.

Detection systems for use on the platforms of the invention include spectroscopic, particularly monochromatic and stroboscopic, and electrochemical detectors (see, for example, Owicki et al., 1992, *Biosensors & Bioelectronics* 7: 255). Spectroscopic methods using these detectors encompass spectroscopy, particularly ultraviolet and visible light absorbance, chemiluminescence, and fluorescence spectroscopy. The detection systems utilizing the detectors of the invention are preferably be external and adjacent to the platform. Generally, the detection systems of the invention comprise a light source and a photodetector, in certain embodiments (such as chemiluminescence), only the photodetector components are required.

The orientation of these components of the detecting means of the apparatus of the invention will be understood to depend on the nature of the detection or cell accumulation chamber and the construction thereof. For example, platforms wherein the detection or cell accumulation chamber comprises an optically transparent surface (completely or in part, see FIGS. 1A and 1C) will advantageously be used with a device having the light source positioned on one side of the platform and the photodetector positioned on the other side of the platform. In alternative arrangements, the photodetector is arranged directly across from the light source (i.e. at an angle of about 180 degrees, as in FIG. 5A) or more advantageously obliquely across the platform from the light source (i.e. at an angle of between 90 and 180 degrees). In the latter embodiments, the apparatus may also advantageously include a mirror or other means for deflecting the transmitted light to the photodetecting means; however, it will be recognized that such mirrors are not required in embodiments provided for fluorescence detection.

Figure 1B:
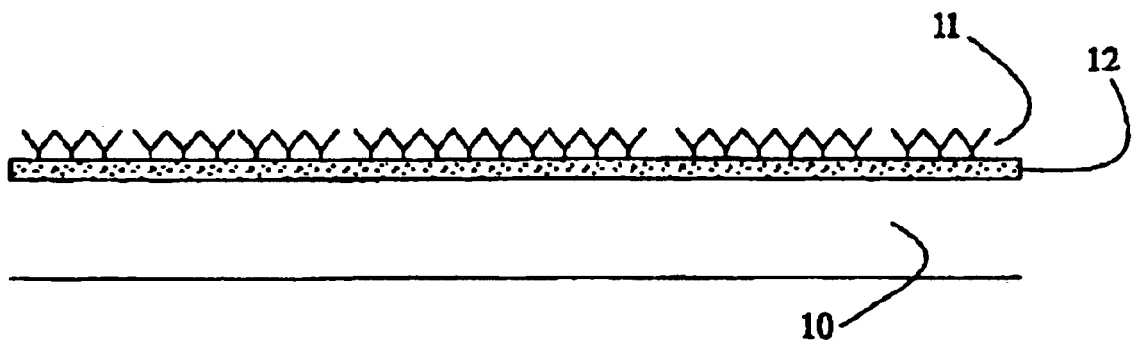
FIG. 1B illustrates a substrate 10 coated with a reflective material 12, which is coated with a specific binding reagent comprising a first member of an affinity binding pair 11.
Figure 1C:
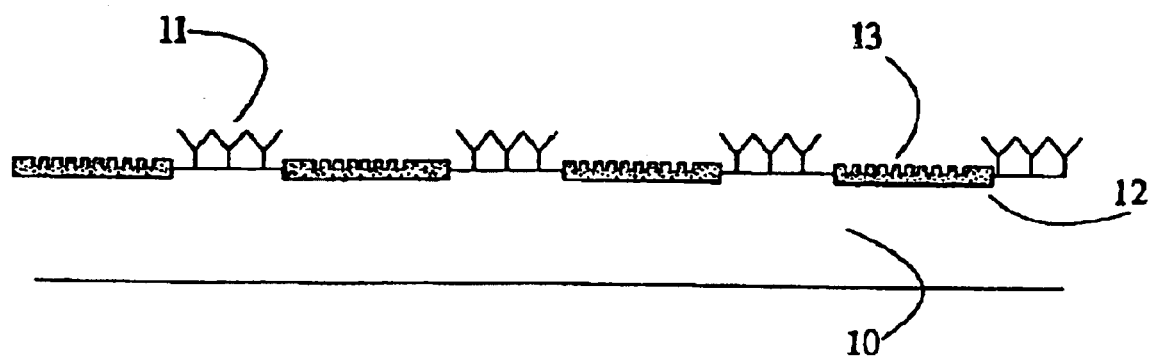
FIG. 1C is a substrate 10, where the surface of the substrate is partially coated with a specific binding reagent comprising a first member of an affinity binding pair 11, and with a patterned reflective material 12 which is in turn derivatized with a blocking agent 13.
Figure 1D:
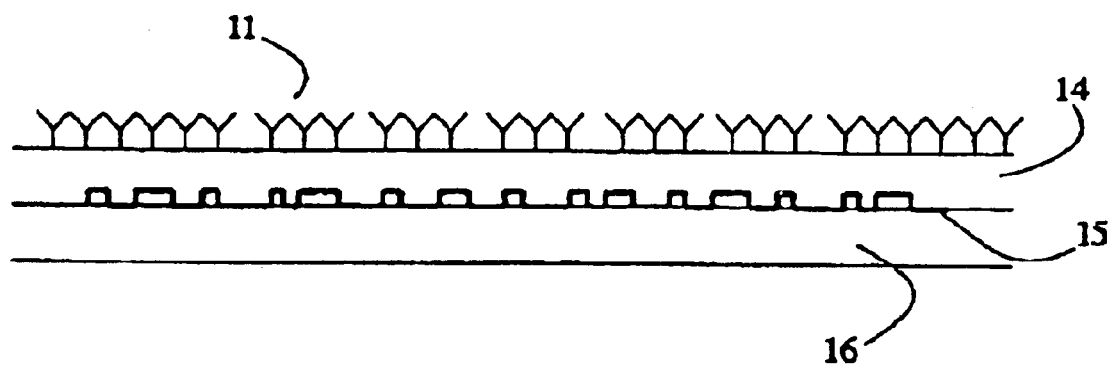
FIG. 1D is a substrate 14, into which has been formed pits carrying encoded information. The lower surface of 14 is coated with a reflective coating 15, and a protective layer 16. The upper surface of 14 is coated with a specific binding reagent comprising a first member of an affinity binding pair 11.

In alternative arrangements, wherein the surface of the platform at the detection or cell accumulation chamber comprises a reflecting surface FIGS. 1B and 1D), the photodetector is advantageously positioned on the same side of the platform as the light source (FIG. 5C). In preferred embodiments, the photodetector is provided as an integrated component of an assembly comprising the light source FIGS. 5D and 5E), wherein the reflected light is detected along the same axis as the incident light (i.e. at about 0 degrees).

The photodetectors of the invention are optimally provided to detect optical absorbance/transmittance, fluorescence, light-scattering or other optical signals, which are processed and translated into data on the position, number and viability of cells on the platform. Embodiments of such platforms and devices comprising scanning arrays are also provided. Also advantageously provided by the invention are detecting means for tracking and focusing the light source on the surface of the platform, and actuating means for positioning the light source on the surface of the platform.

Figure 6A:
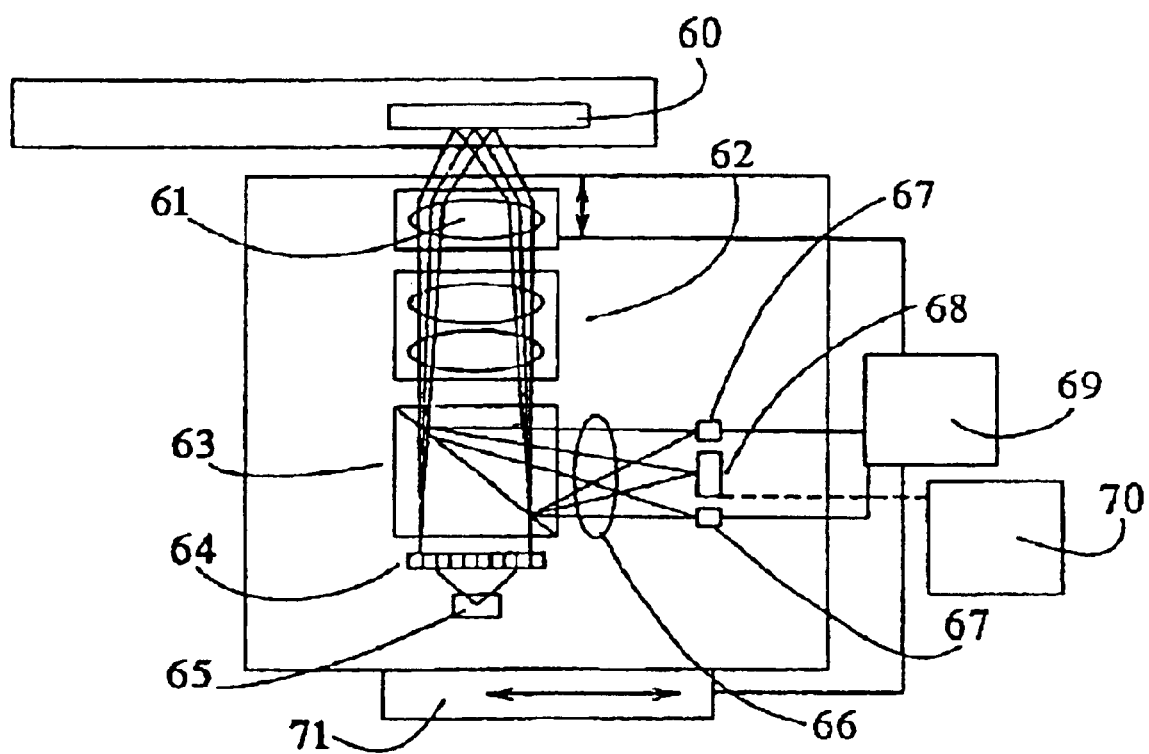
FIG. 6A illustrates an optical apparatus or "head" derived from optical memory storage and retrieval devices for interrogating a platform 60. Optical components include diode laser 65, diffraction grating 64, beam splitter 63, collimating lenses 62, focusing lens and actuator 61, lens 66, side lobe detectors 67, and central detector 68. Focusing and tracking are achieved through servo control circuits 69, and actuators 61 and 71. The signal derived from interaction of the central beam with the cell 74 (e.g. fluorescence emission) is detected by optical detector 68 and amplified by circuitry 70.
Figure 6B:
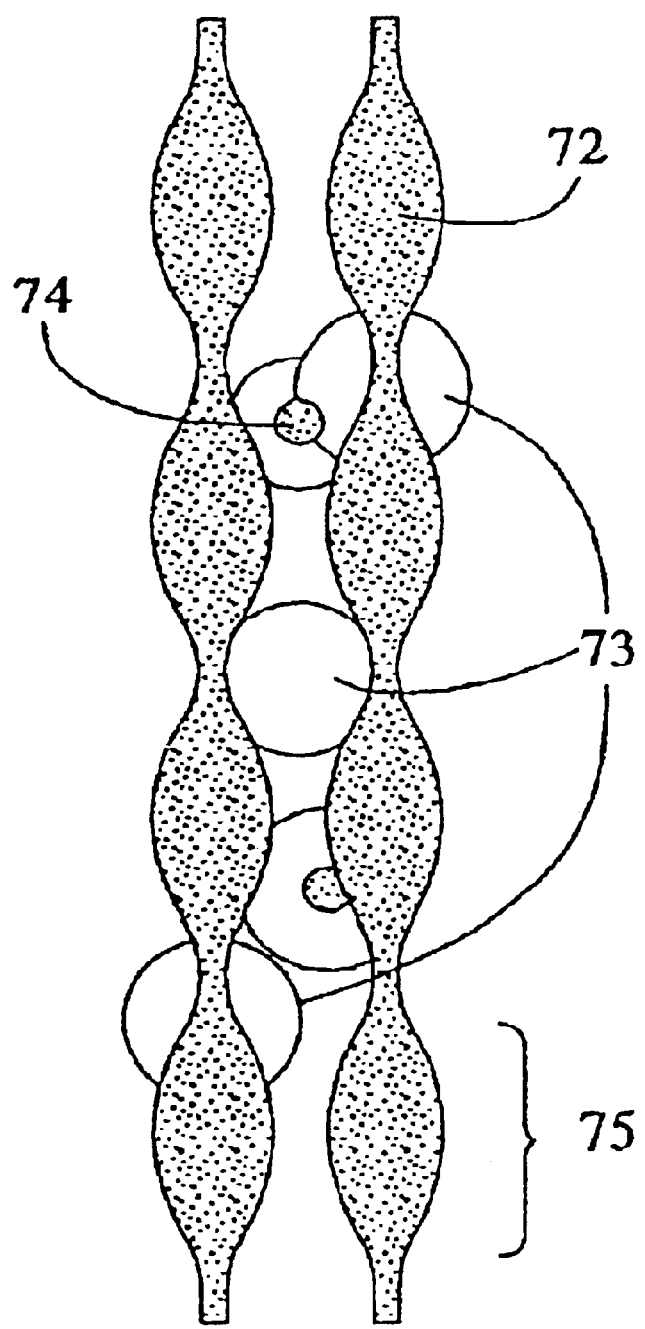
FIGS. 6B and 6C illustrate advantageous arrangements of reflective tracking features on the platform.
Figure 6C:
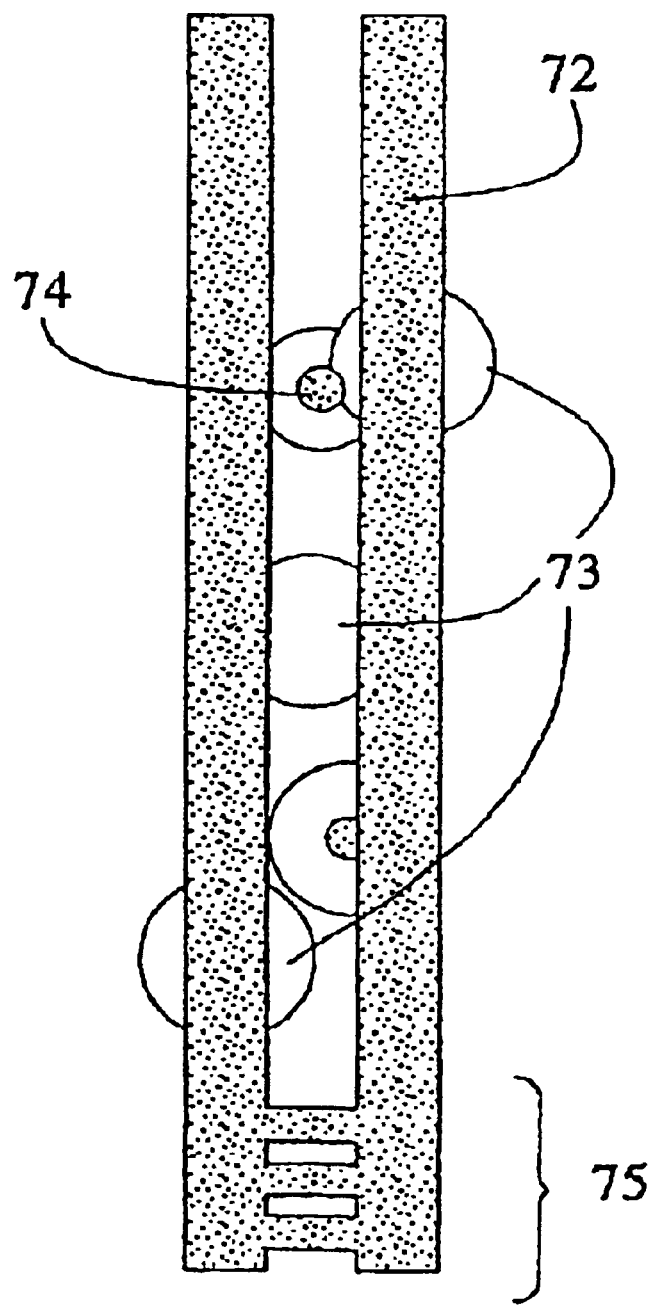
Figure 7:
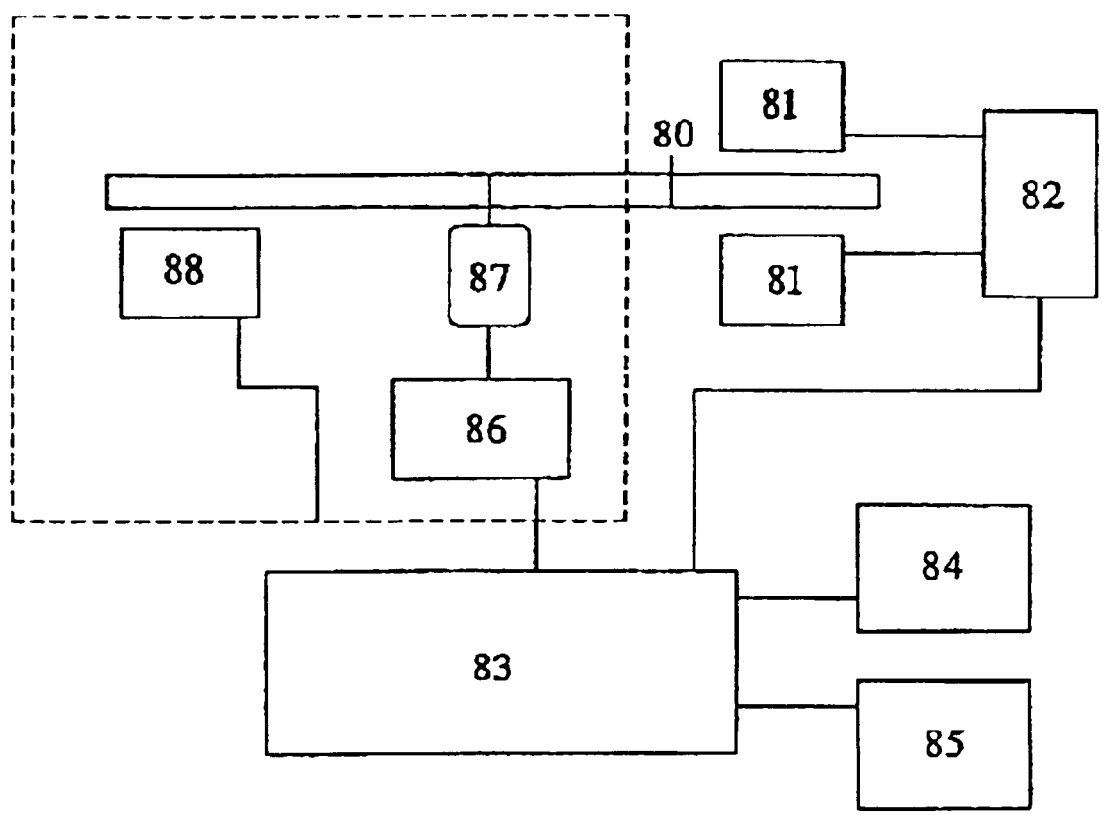
FIG. 7 illustrates an apparatus for utilizing the platforms of the invention. Optical detection systems 81, such as those illustrated in FIG. 5, are linked to controlling circuitry 82. Output signals are measured by the microcontroller 83, which processes the data and communicates results through a user interface 84 and/or stores the data in local or nonlocal memory 85 through remote data links. Rotatable platforms require the use of a motor 87 and motor control circuitry 86, and may also include optical data retrieval and storage means 88.

Detecting means derived from conventional CD or CD-ROM systems are also advantageously provided. The apparatus 56 in FIG. 5E represents an optical "head" of a CD (see E. W. Williams, 1994, *The CD-ROM and Optical Disc Recording Systems,* Oxford University Press, New York) and is used with the platform of FIG. 1D, the substrate of which contains data encoded in an industry standard format, in the form of pits stamped into the plastic matrix and coated with a reflective coating (e.g., aluminum). The platform is constructed so that the aluminized pits are the focal point of the CD laser. Platform fluidics handling components are built within and upon this plastic layer. Particulates bound through the first member of the binding pair 11 to the surface of the thinner substrate 14 scatter light and interfere with the reading of the data. Those skilled in the art recognize that the thickness and index of refraction of optical storage media (e.g. CD-ROM) are such that the effect of light scattering by particles on the surface of the disk is reduced. In this application, the thickness and composition of the substrate, fluid layer and cover are chosen such that particulates bound to the surface interfere with the integrity of the data, and the errors generated in reading the data provide a measure of the number of particulates bound. The optical detection apparatus pictured in FIG. 5D and in more detail in FIG. 6A, is to be used with the platform of FIG. 1C which contains reflective features such as those pictured in FIG. 6B and 6C. Optical elements similar to those used in a conventional CD head are used to generate and focus a main beam and side beams on the surface of the platform. The reflection of the side beams off of the reflective features are used to track the central beam along the transparent regions of the platform, so that particulates bound there may be detected. Those skilled in the art recognize that optical data retrieval systems use the reflection of the central beam in a servo-controlled focusing system. This approach differs in that control of the focusing actuator is based on intensities of the reflections from the side beams off of the reflective features. The interaction of a particle with the central beam may result in fluorescence, absorption, or scattering, which may be detected by the detector 50 within the "head" or by another detector advantageously placed (not shown). These embodiments thus provide cell sorting capability, cell tracking and cell viability information, whereby the status of the cells at each point can be detected and distinguished from each other cell. This capacity enables the platforms and devices of the invention to provide cell-specific data and tracking information.

Preferred spectroscopic methods include fluorescence, whereby fluorescence detector systems developed for macroscopic uses are adapted for use with the platforms of this invention. For example, an excitation source such as a laser is focused on an optically-transparent section of the disk. Light from any analytically-useful portion of the electromagnetic spectrum can be coupled with a platform material that is specifically transparent to light of a particular wavelength, permitting spectral properties of the light to be determined by the dye or other reagent used to illuminate a particulate retained in an detection chamber or cell incubation chamber or surface or specialized section of the platform interrogated by illumination with light. Alternatively, the selection of light at a particular wavelength can be paired with a material having geometries and refractive index properties resulting in total internal reflection of the illuminating light. This enables either detection of material on the surface of the disk through evanescent light propagation, or multiple reflections through the sample itself, which increases the path length considerably.

In the practice of this aspect of the invention, the outer surface of a waveguide (a fiber optic, a prism, etc.) is coated with the first member of a binding molecule pair. Particles which express the second member of the pair on their surface(s) are then introduced to the fluid which is in contact with the optical waveguide. A sufficient time is allow to pass so that the particles may bind through the binding pair to the outer surface of the waveguide. (Gentle agitation of the fluid may speed up this process.) The waveguide is then washed with buffer. Light is transmitted through the waveguide from a source to a photodetector. Light within the waveguide engages in multiple internal reflection as it passes along the waveguide. It is well known that there is also an evanescent wave penetrating slightly past the surface of the waveguide and into the surrounding fluid. Particles adsorbed to the surface of the waveguide will both scatter and absorb light in this evanescent wave. The amount by which the radiation transmitted to the detector is depressed relative to "clean" waveguides can be used to infer the number of adsorbed particles.

In one example of fluorescence detection using the platforms of the invention, light of both the fluorescence excitation wavelength and the emitted wavelength are guided through one face of the device. An angle of from about 90° to about 180° is used to separate the excitation and collection optical trains, more preferably an angle of about 135° to position the detector obliquely from both the edge of the platform and the direction of the light from the light source. It is also possible to use other angles, including 0 degrees, whereby the excitation and emitted light travels collinearly. As long as the source light can be distinguished from the fluorescence signal, any optical geometry can be used. Optical windows suitable for spectroscopic measurement and transparent to the wavelengths used are included at appropriate positions (i.e., in detection chamber or cell accumulation chambers or surfaces or other specialized sections of the platform). The use of this type of fluorescence has been disclosed by Haab et al. (1995, Anal. Chem. 67: 3253–3260).

Configurations appropriate for evanescent wave systems can provide for fluorescence to be coupled back into a waveguide on the platform, thereby increasing the efficiency of detection. In these embodiments, the optical component preceding the detector can include a dispersive element to permit spectral resolution. Fluorescence excitation can also be increased through multiple reflections from surfaces in the device whenever noise does not scale with path length in the same way as with signal.

Absorbance measurements can be used to detect a dye or stain, such as a vital stain, or other analyte that changes the intensity of transmitted light by specifically absorbing energy (direct absorbance) or by changing the absorbance of another component in the system (indirect absorbance). Absorbance measurements are preferably used in conjunction with enzyme-linked detection of the presence of a particulate within a detection chamber of cell accumulation chamber or a surface or specialized section of the platform. In preferred embodiments, cellular particulates are detected by vital staining or other cell-specific staining (such as the use of dyes specific for certain cell types). Optical path geometry is designed to ensure that the absorbance detector is focused on a light path receiving the maximum amount of transmitted light from the illuminated sample. Both the light source and the detector are advantageously positioned external and adjacent to the platform; in rotatable embodiments of the platforms of the invention, the light source and the detector can be moved in synchrony with the platform, or more preferably, the light source illuminates the platform stroboscopically so that absorbance/transmittance is sampled in synchrony with rotation of the platform and cyclical positioning of the detection or cell accumulation chamber with the solitary position of the light source/detector pair. The detection chamber or cell accumulation chamber, or a surface or other specialized section of the platform can constitute a cuvette that is illuminated wherein transmitted light detected in a single pass or in multiple passes, particularly when used with a stroboscopic light signal that illuminates the detection chamber at a frequency equal to the frequency of rotation or multiples thereof. Alternatively, the detection chamber can be a planar waveguide, wherein the analyte interacts on the face of the waveguide and light absorbance is the result of attenuated total internal reflection (i.e., the analyte reduces the intensity source light if the analyte is sequestered at the surface of the chamber, using, for example, specific binding to a compound embedded or attached to the chamber surface; see Dessy, 1989, Anal. Chem. 61: 2191). Although preferred embodiments of absorbance/transmittance detector arrays are advantageously used with platforms of the invention comprising an optically transparent surface (permitting a direct light path through the surface of the platform an positioning of the light source and detector on opposite sides of the platform), alternative embodiments wherein the detector is positioned obliquely to the light source, or other embodiments wherein the surface of the platform comprises a reflective surface and the detector and the light source are positioned on the same side of the platform are also envisioned and encompassed in this description of the invention. Both the light source and the detector are advantageously positioned external and adjacent to the platform; in rotatable embodiments of the platforms of the invention, the light source and the detector can be moved in synchrony with the platform, or more preferably, the detector output is sampled periodically to so that the absorbance/transmittance is measured.

Indirect absorbance can be used with the same optical design. For indirect absorbance measurements, the analyte does not absorb the source light; instead, a drop in absorbance of a secondary material is measured as the analyte displaces it in the sample chamber. Increased transmittance therefore corresponds to analyte concentration. This detection schema is advantageously used in embodiments of the invention wherein the effect of a test compound on a cell is determined, wherein the detectable analyte is displaced by a metabolite or other molecule produced by the cell in response to the presence of the test compound.

Light scattering and turbidity can also be measured on the platform. Optics are configured as described for absorbance measurements. In this analysis, the intensity of the transmitted light is related to the concentration of the light-scattered particles in a sample. Monochromatic light from a light source, advantageously a laser light source, is directed across the cross-sectional area of a detection chamber or cell accumulation chamber on the platform. Light scattered by particles in a sample, such as cells, is collected at several angles over the illuminated portion of the chamber (see Rosenzweig et al., 1994, Anal. Chem. 66: 1771–1776). Data reduction is optimally programmed directly into the device based on standards such as appropriately-sized beads to relate the signal into interpretable results. Using a calibrated set of such beads, fine discrimination between particles of different sizes can be obtained.

In alternative arrangements, wherein the surface of the platform at the detection or cell accumulation chamber comprises a reflecting surface, the photodetector is advantageously positioned on the same side of the platform as the light source. In preferred embodiments, the photodetector is provided as an integrated component of the light source, wherein the reflected light is detected along the same axis as the incident light (i.e. at about 0°).

It will be understood that the light source supplied with the devices of the invention will also be supplied with focusing means and optical elements to focally illuminate the platform. It will also be recognized that the photodetectors supplied with the devices of the invention will be supplied with light collecting means, including mirrors and other optical elements to direct the transmitted, reflected or fluorescent light from the detection or cell accumulation chamber to the photodetector.

Electric potential measurement can also be used for detecting the presence of a particulate, especially a cell and preferably a microbial cell, on a surface or in a chamber comprising a specific binding reagent. In these embodiments of the invention, microelectrodes are fabricated of a noble metal, preferably gold or platinum, using conventional techniques and are imbued with a biological specificity by impregnating or coating the electrodes with a specific binding reagent. Electropolymerization of organic films, such as polypyrrole or polyalanine, comprising said specific binding reagent, or electrochemical reduction of thiol-terminated specific binding reagents can be used to fashion such specific electrodes. Detection of the presence or absence of cellular and other particulates is achieved by measuring the electrical impedance between one electrode and a solution contact, which can advantageously be positioned in contact with the fluid in the detection chamber comprising the electrodes. Measurements are made using alternating voltages at frequencies from about 10 Hz to 1 MHz. Impedance readings are analyzed by a reading device comprising a microprocessor to determine detection of the presence or absence of cells and other particulates.

Temperature control elements-are provided to control the temperature of the platform during incubation of a fluid containing a particulate, most advantageously used to facilitate specific binding between the particulate and the specific binding reagent. A preferred temperature is room or ambient temperature, although temperatures above ambient (e.g., 37° C.) and below ambient (e.g. 20° C.) are also preferred. Temperature control is also important for embodiments of the invention used to detect particulates that are cells; in these embodiments, the temperature is advantageously kept below 42° C. and above 4° C. to protect the integrity and viability of the cells. The invention therefor provides heating elements, including heat lamps, direct laser heaters, Peltier heat pumps, resistive heaters, ultrasonication heaters and microwave excitation heaters, and cooling elements, including Peltier devices and heat sinks, radiative heat fins and other components to facilitate radiative heat loss. Thermal devices are preferably arrayed to control the temperature of the platform over the area of the detection or cell accumulation chamber or surface, although arrangements whereby the platform temperature as a whole is controlled are also preferred. Preferably, heating and cooling elements comprise the device of the invention, although certain elements, such as radiative heat transfer "fins" and other such components may comprise the platforms of the invention. The temperature of any particular area on the platform (preferably, the detection chamber or surface) is monitored by resistive temperature devices (RTD), thermistors, liquid crystal birefringence sensors or by infrared interrogation using IR-specific detectors, and can be regulated by feedback control systems.

Filters, sieving structures and other means for selectively retaining or facilitating passage of particulate matter, including cells, cell aggregates, protein aggregates, or other particulate matter comprising fluids applied to a platform of the invention are provided. Such filtering means include micro-sieving structures that are fabricated directly into a fluid handling structure on a platform (e.g., U.S. Pat. No. 5,304,487; International Application, Publication No. WO93/22053; Wilding et al., 1994, *Automat. Analyt. Tech.* 40: 43–47) or fabricated separately and assembled into the fluid handling structures. The sieving structures are provided with a range of size exclusion orifices and are optionally arranged sequentially so as to fractionate a sample based upon the sizes of the constituent parts of the sample. Preferably, such sieving structures are provided to permit the introduction of specific particulates into the detection chamber or surface (such as a cell, preferably a microbial cell) while excluding protein aggregates or other non-specific particle-like constituents of a fluid which could interfere with detection of the particular particulates of interest. Specifically included in such sieving structures are reagents such as beads and particularly beads coated with a compound such as an antibody having an affinity for a contaminant or other substance that would interfere with the assay to be performed. Also provided in certain embodiments of the cell accumulation chamber of the platforms of the invention are filtering means having a pore size sufficiently chosen to prevent the cells in the chamber from being lost upon evacuation of the chamber of the fluid contents thereof, or during fluid replacement, e.g., by a wash buffer.

Figure 4A:
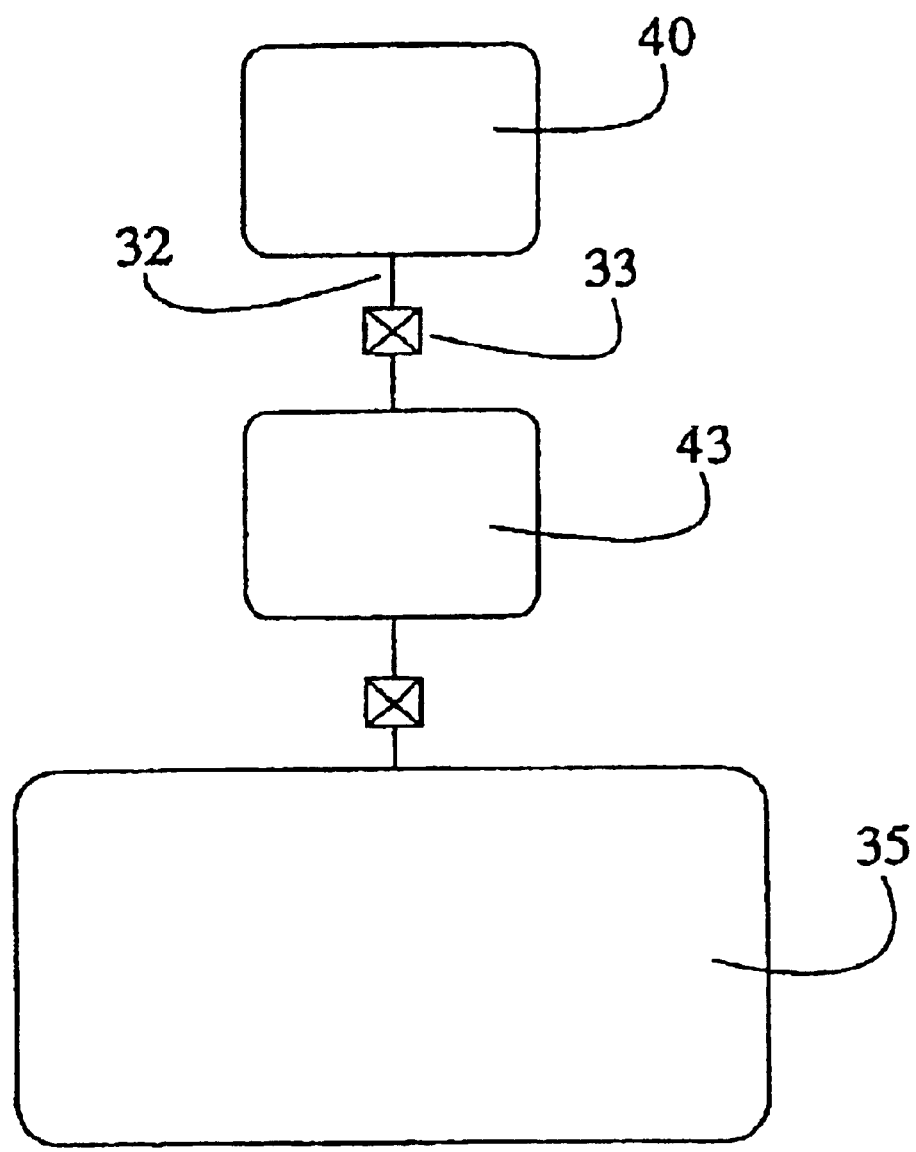
FIG. 4A comprises a test molecule chamber 40, linked by a capillary 32 containing a valve 33 to a cell accumulation chamber 43. The binding chamber is linked to a waste chamber 35.
Figure 4B:
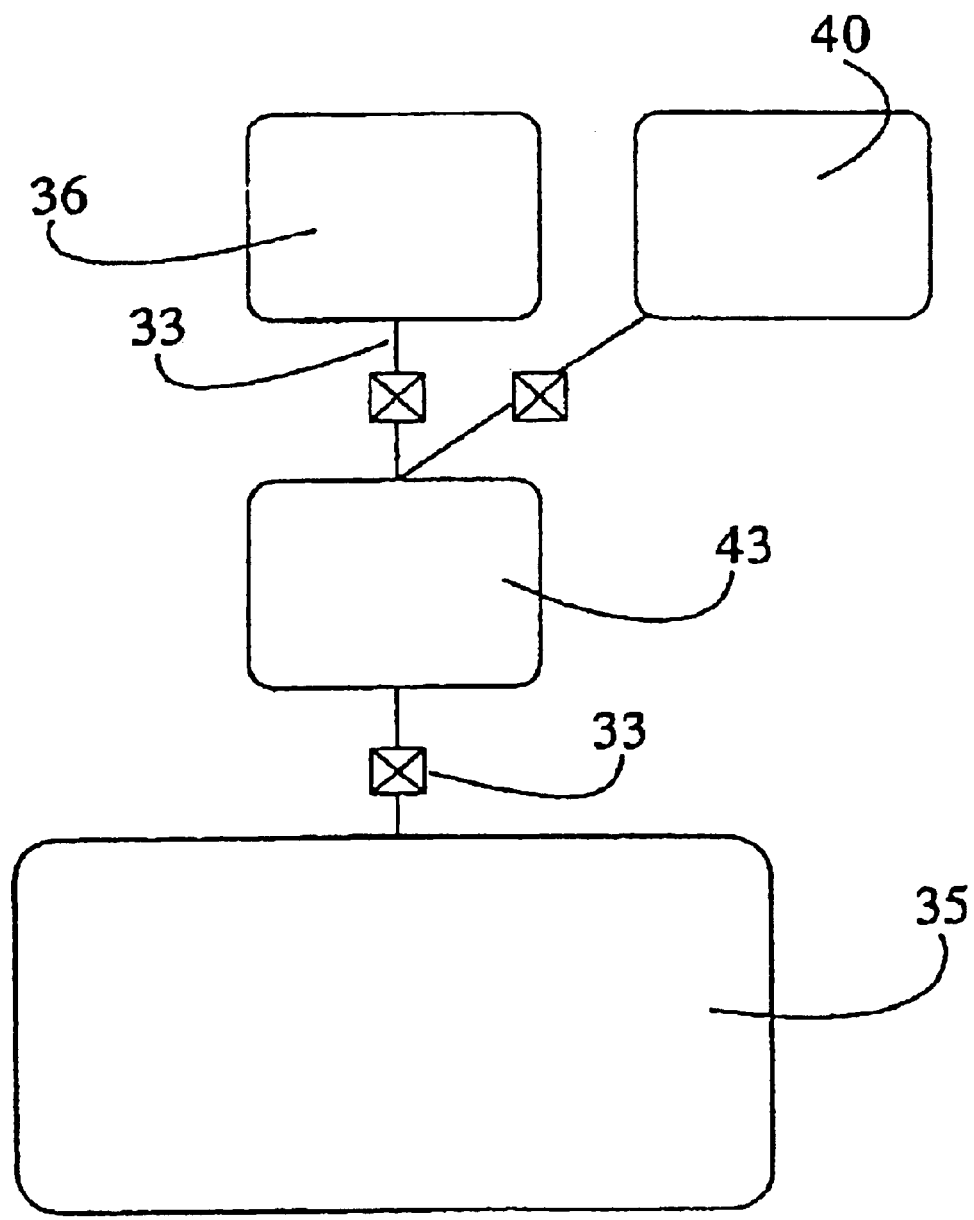
FIG. 4B incorporates a dye chamber 36 fluidically connected via a capillary 32 and valve 33 to the binding chamber 34.
Figure 4C:
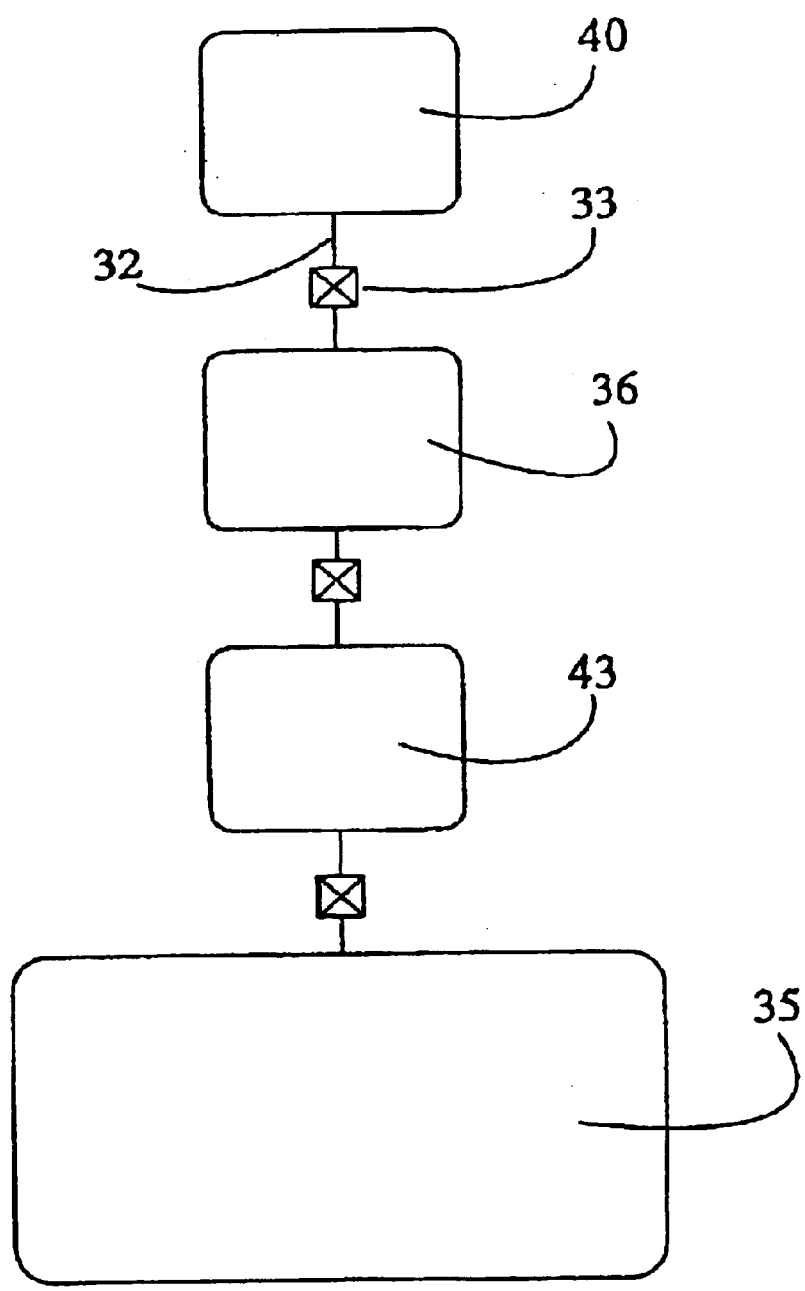
FIG. 4C provides an alternate arrangement of the components of FIG. 4B.
Figure 4D:
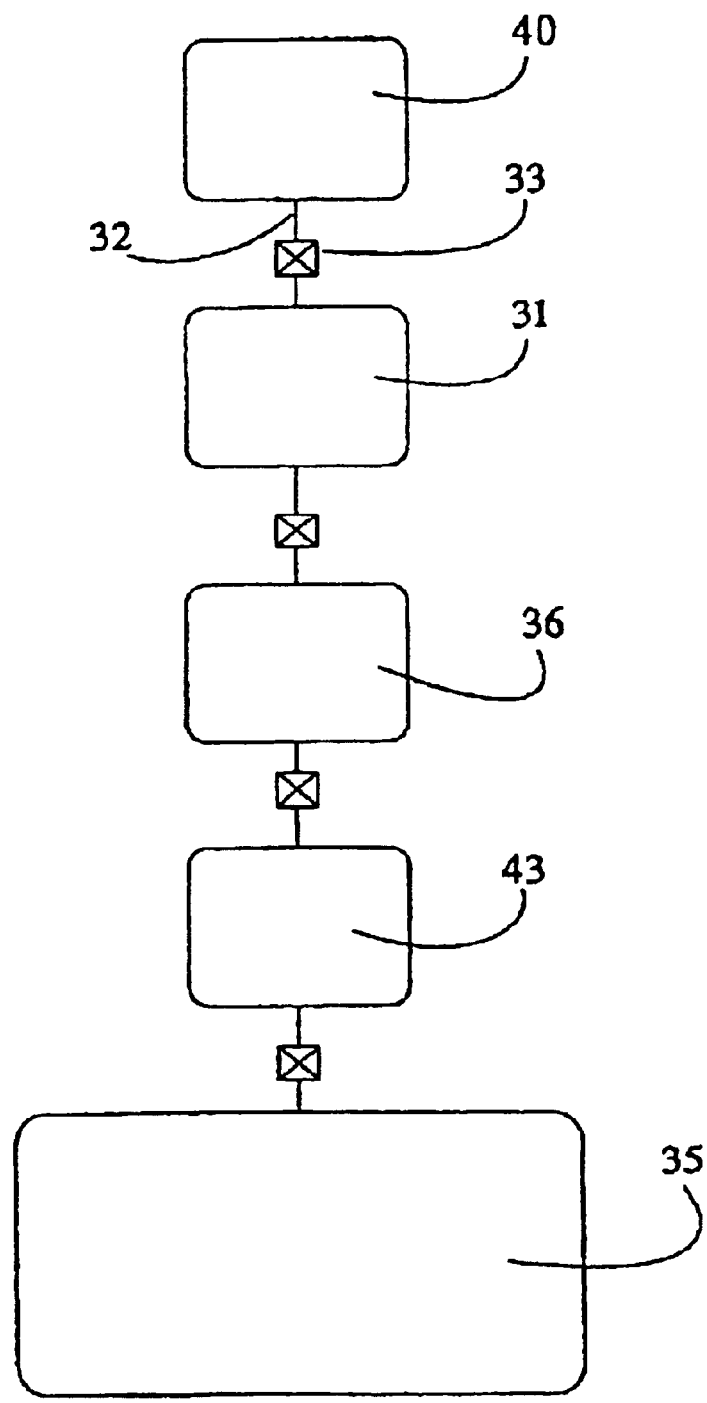
FIG. 4D is similar to FIG. 4C, but with the incorporation of a wash buffer chamber 31 in the fluidic path between the test molecule chamber 40 and the cell accumulation chamber 43.
Figure 4E:
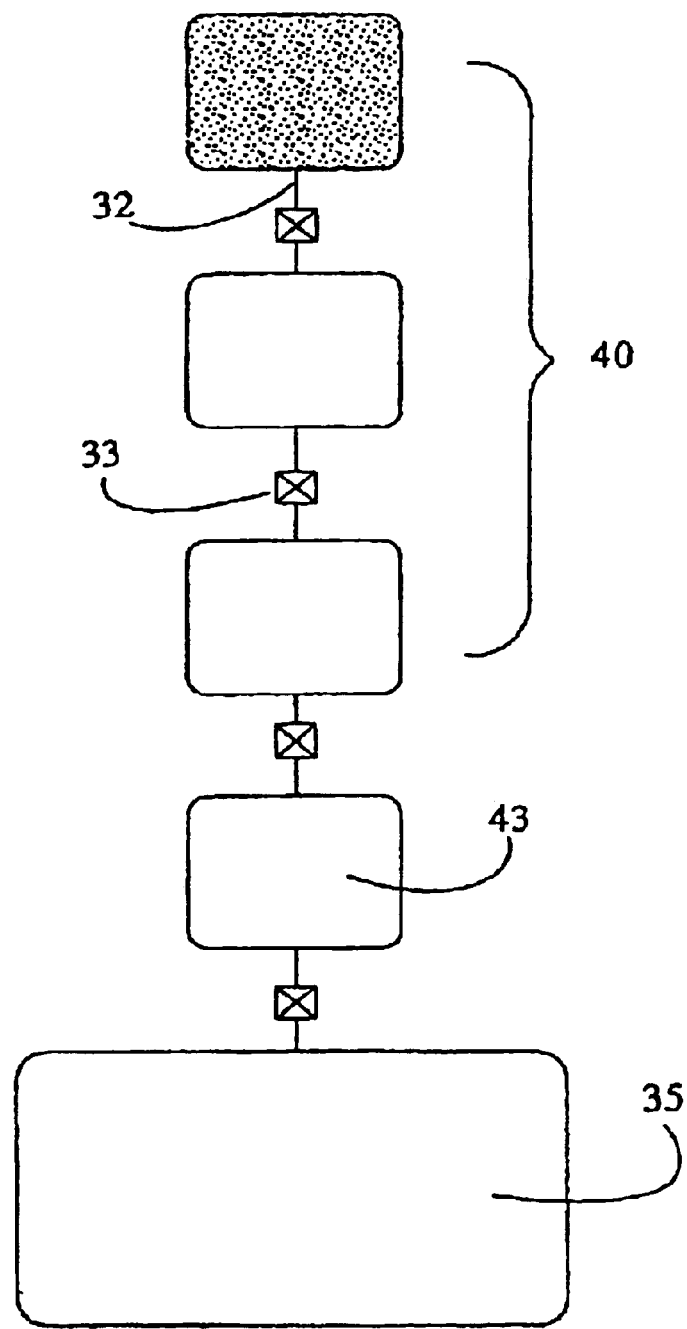
FIGS. 4E and 4F are similar to FIG. 4A, with the exception of a multiplicity of test molecule chambers 40 arrayed serially (4E) or in parallel (4F).
Figure 4F:
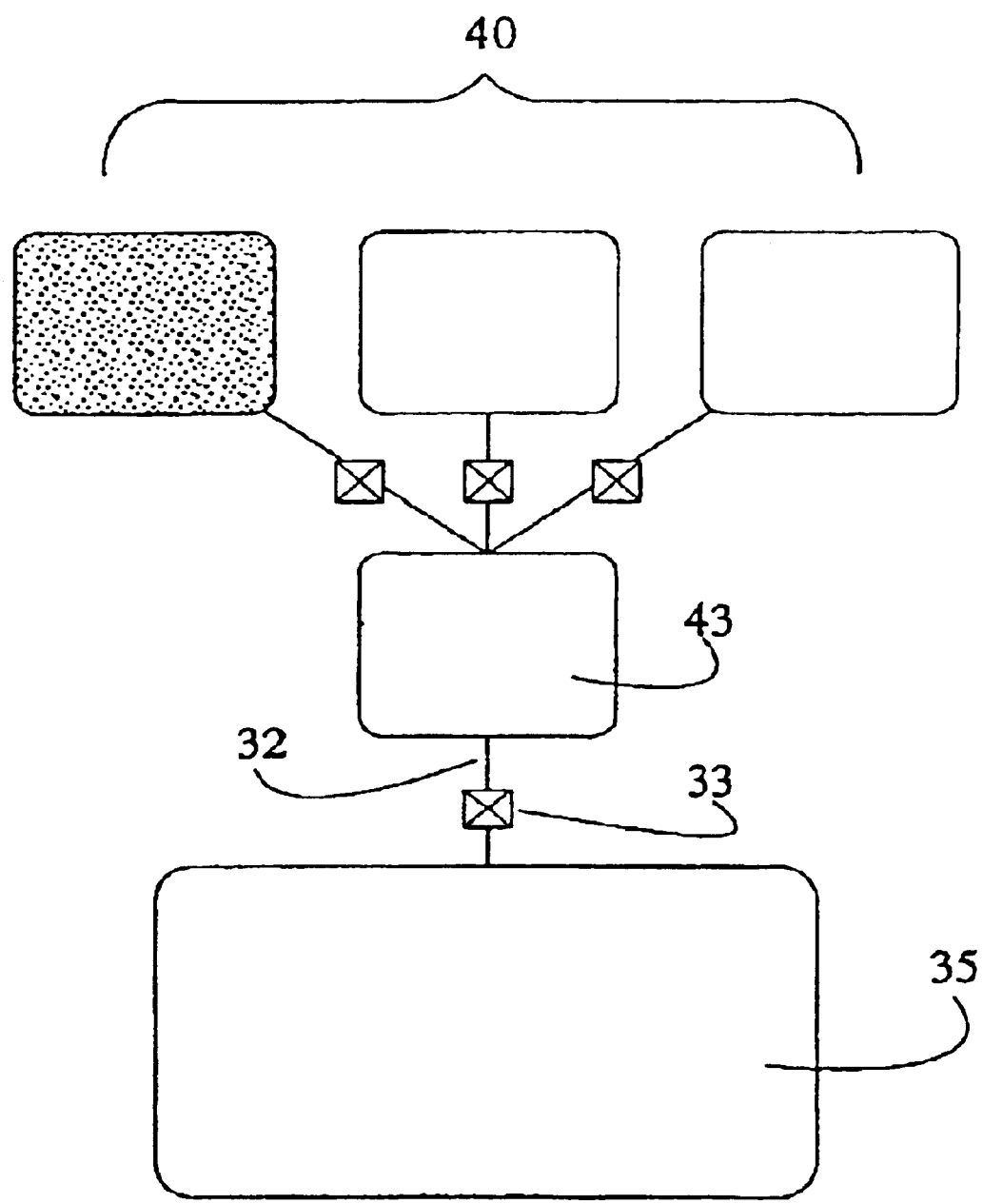
Figure 4G:
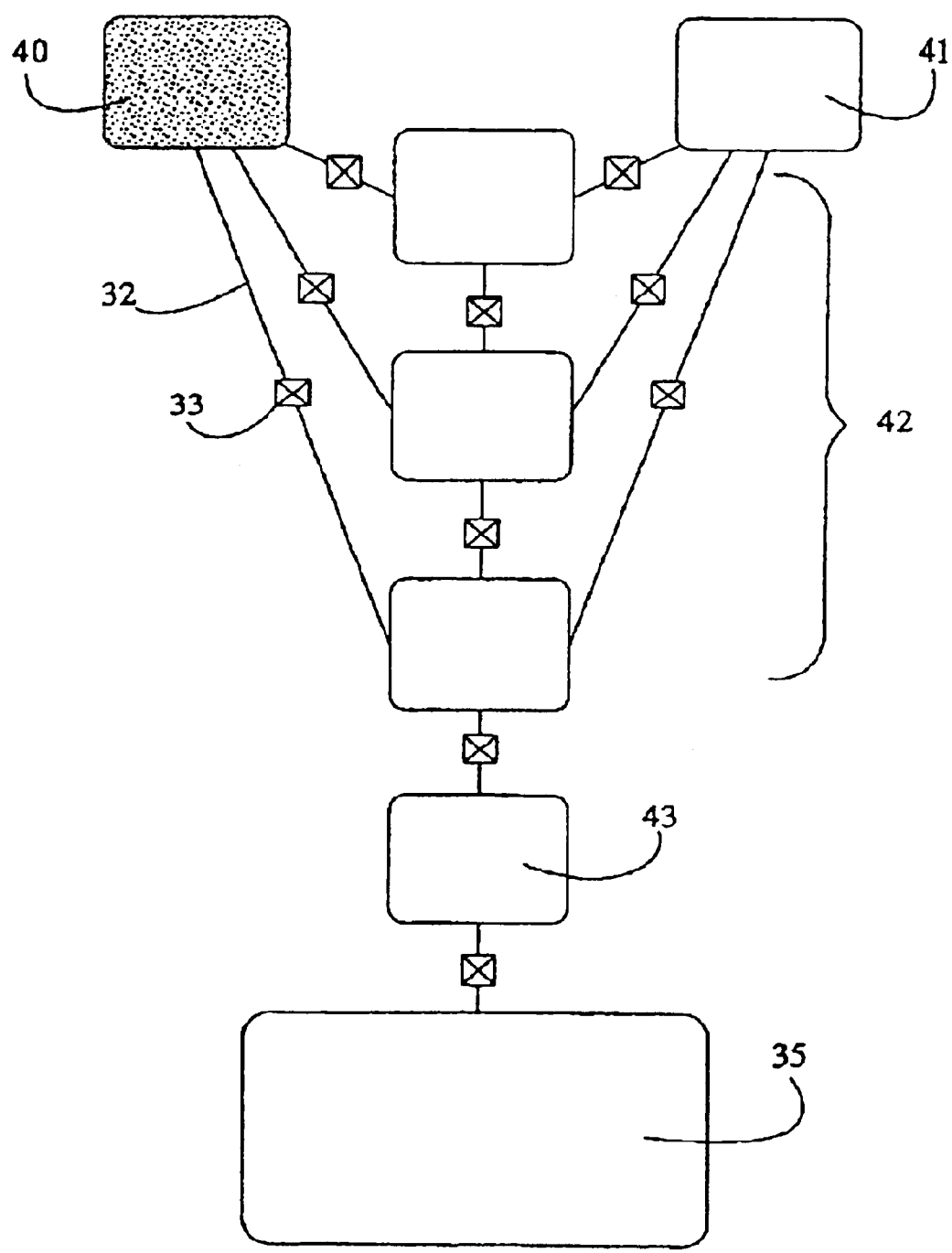
FIG. 4G is an arrangement in which fluid from a test molecule chamber 40 and a dilution buffer reservoir can be directed to receiving chambers 42 to provide serial dilutions of the test molecule solution.
Figure 4H:
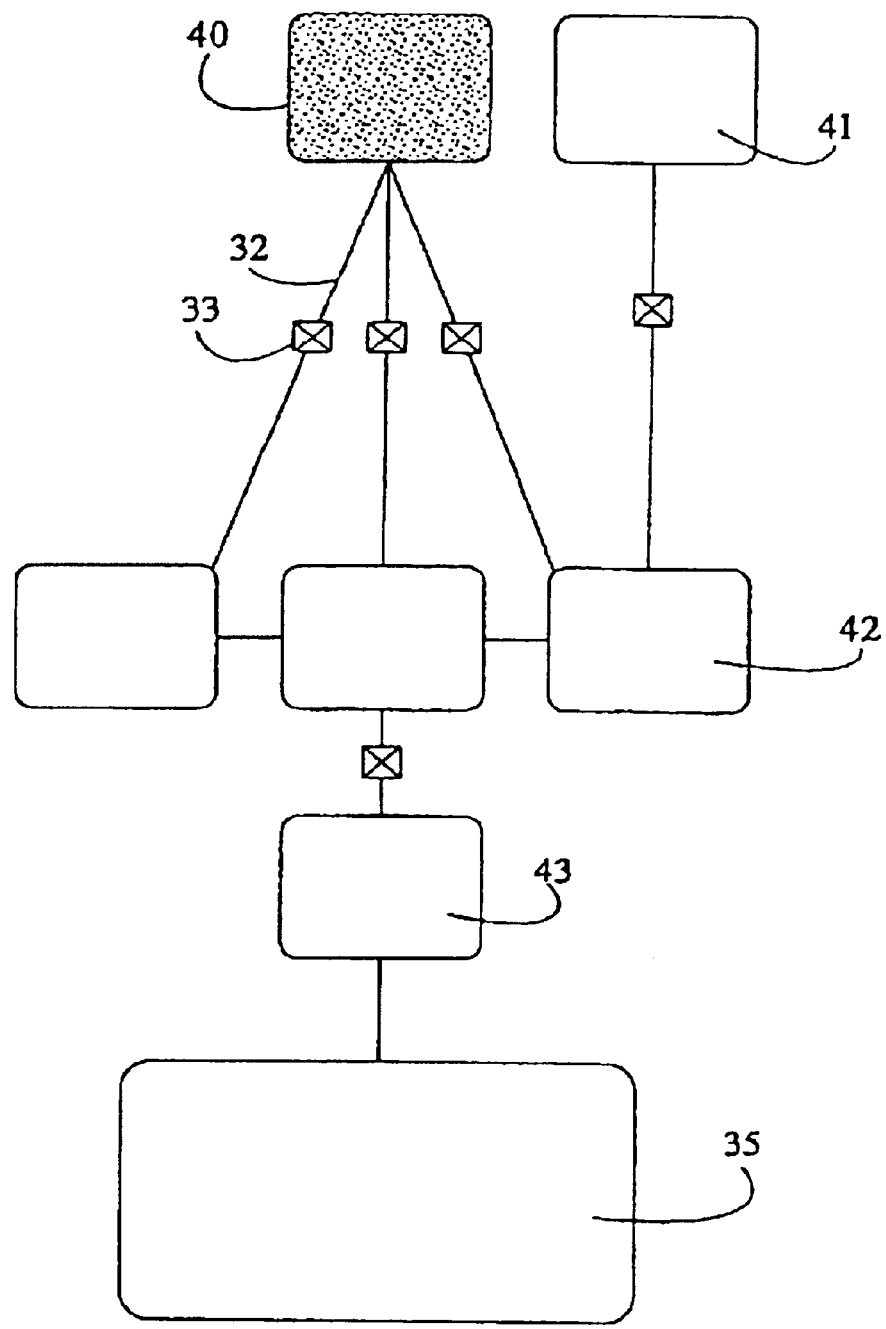
FIG. 4H is another advantageous arrangement of the components of FIG. 4G.

Mixing elements, are also advantageously provided as components of the platforms of the invention. Static mixers can be incorporated into fluid handling structures of the platform by applying a textured surface to channels or chambers composing the mixer. Two or more channels can be joined at a position on the platform and their components mixed together by hydrodynamic activity imparted upon them by the textured surface of the mixing channel or chamber and, for example, by the action of centripetal force imparted by a rotating platform. Fluids can be mixed for the purposes of preparing serial dilutions of test compounds for subsequent transfer to the cell accumulation chamber, as is illustrated schematically in FIGS. 4G and 4H. Mixing can also be accomplished by rapidly changing the direction of rotation and by physically agitating the platform by systems external thereto.

Also provided as components of the apparatus of the invention are devices for manipulating the platforms of the invention and to provide components for control of the operation of the platform, to provide detection means and data acquisition and storage means.

In embodiments of the invention comprising rotatable disks, the device is a disk player/reader that controls the function of the disk. This device comprises mechanisms, spindles and motors that enable the disk to be loaded and spun, whereby fluid movement is centripetally-motivated as a consequence (i.e., the centripetal acceleration of the rotating disk causes the fluid to move through the microchannels and in the other fluidic components of the platform). In addition, the device provides means for a user to operate the disk and access and analyze data, preferably using a keypad and computer display.

Integrated electronic processing systems (generally termed "controllers" herein) that include microprocessors and I/O devices provide the controlling elements of the platforms of the invention. Such elements can be fabricated directly onto a platform, but are more preferably and most advantageously placed off the platform as a component of the device provided in combination with the platform to comprise the apparatus of the invention. In preferred embodiments of the apparatus of the invention, the controllers can be used to control the rotation drive motor (both speed, duration and direction), system temperature, optics, data acquisition, analysis and storage, and to monitor the state of systems integral to the platform. Examples of advantageous controlling means are provided in U.S. Ser. No. 08/768,990, filed Dec. 18, 1996, incorporated by reference herein.

Specific examples of rotational controllers are those using rotation sensors adjacent to the motor itself for determining rotation rate, and motor controller chips (e.g., Motorola MC33035) for driving direction and speed of such motors. Such sensors and chips are generally used in a closed-loop configuration, using the sensor data to control rotation of the disk to a rotational set-point. Similarly, the rotational data from these sensors can be converted from a digital train of pulses into an analog voltage using frequency-to-voltage conversion chips (e.g., Texas Instruments Model LM2917). In this case, the analog signal then provides feedback to control an analog voltage set-point corresponding to the desired rotation rate. Controllers may also use the data encoded in the disk's data-carrying surface in a manner similar to that used in commercially-available compact disk (CD) players. In these embodiments, the digital data read by the laser is used to control rotation rate through a phase-locked loop. The rotation rate information inherent in the frequency of data bits read may be converted to an analog voltage, as described above.

The controllers can also include communication components that allow access to external databases and modems for remote data transfer. Specifically, controllers can be integrated into optical read systems in order to retrieve information contained on the disk, and to write information generated by the analytic systems on the disk to optical data storage sections integral to the disk. In these embodiments it will be understood that both read and write functions are performed on the surface of the disk opposite to the surface comprising the components disclosed herein.

Information (i.e., both instructions and data, collectively termed "informatics") pertaining to the control of any particular analytic system on the disk can be stored on the disk itself or externally, most advantageously by the microprocessor and/or memory of the device of the invention, or in a computer connected to the device. The information is used by the controller to control the timing and open/closed state of microvalves on the platform, preferably a disk, to determine optimal disk rotational velocity, to control heating and cooling elements on the disk or comprising the device, to monitor detection systems, to integrate data generated by the disk and to implement logic structures based on the data collected.

Such informatics controllers are also advantageously provided in devices used with embodiments of the platforms of the invention not related to rotatable platforms.

In one aspect of the invention is provided a device for manipulating the platform of the invention and that advantageously accesses and writes information or initiate processes on the platform. These include the mechanical drive and circuitry for rotation monitoring and control, overall system control, data read/write devices, external detectors and actuators for use with the platform, dedicated data and assay processors for processing encoded data and assay data, a central processor unit, a user interface, and means for communicating to the platform, the user, and other devices. Mechanical drive and associated circuits include devices to control and monitor precisely the rotation rate and angular position of the platform, and devices to select and mount multiple-disks from a cassette, turntable, or other multiple-disk storage unit. System control units provide overall device control, either pre-programmed or accessible to the user-interface. Data read/write devices are provided for reading encoded information from the platform. The device can also include external actuators comprising optical magneto-optic, magnetic and electrical components to actuate microvalves and initiate processes on the platform, as well as external detectors and sensors or components of detectors and sensors that operate in concert with other components, including analytic and diagnostic devices.

Components of the devices comprising the apparatus of the invention include the mechanical drive and circuitry for rotation monitoring and control, overall system control, data read/write devices, external detectors and actuators for use with the disk, dedicated data and assay processors for processing encoded data and assay data, a central processor unit, a user interface, and means for communicating to the disk, the user, and other devices. Mechanical drive and associated circuits include devices to control and monitor precisely the rotation rate and angular position of the disk, and devices to select and mount multiple-disks from a cassette, turntable, or other multiple-disk storage unit. System control units provide overall device control, either pre-programmed or accessible to the user-interface. Disk data read/write devices are provided for reading encoded information from a disk or other medium. Optimally, write-to-disk capabilities are included, permitting a section of the disk to contain analytical data generated from assays performed on the disk. This option is not advantageous in uses of the disk where the disks are contaminated with biological or other hazards, absent means (such as sterilization) for neutralizing the hazard. The device can also include external actuators comprising optical magneto-optic, magnetic and electrical components to actuate microvalves and initiate processes on the disk, as well as external detectors and sensors or components of detectors and sensors that operate in concert with other components on the disk, including analytic and diagnostic devices.

Disk data processors are also advantageously incorporated into the devices of the invention which enable processing and manipulation of encoded disk data. These components include software used by the device CPU, programmable circuits (such as FPGAs, PLAs) and dedicated chipsets (such as ASICs). Also provided are assay processors for processing data arising from events and assays performed on the disk and detected by external detectors or communicated from on-disk components. The device also advantageously comprises a central processing unit or computer which will allow processing of disk data and assay results data-analysis (through pre-programming); additionally, conventional computer capabilities (word-processing, graphics production, etc.) can be provided.

A user interface, including keypads, light-pens, monitors, indicators, flat-panel displays, interface through communications options to host-devices or peripheral devices, and printers, plotters, and graphics devices are provided as components of the platform and devices of the invention. Communication and telecommunications are provided through standard hard-wired interfaces (such as RS-232, MEE-488M SCSI bus), infra-red and optical communications, short- or long-range telecommunications ("cellular" telecommunications radio-frequency), and internal or external modem for manual or automated telephone communications.

Disk information comprises both software written to the disk to facilitate operation of the assays constructed thereupon, and assay data generated during use of the by the user. Disk information includes material written to the disk (as optically encoded data) and information inherent to the disk (e.g., the current status of a valve, which can be accessed through magnetic pickup or through the reflective properties of the coating material at the valve-position) Data written to the disk may include but is not limited to the audio/video/test and machine format information (e.g., binary, binhex, assembler language). This data includes system control data used for initiation of control programs to spin the disk, or perform assays, information on disk configuration, disk identity, uses, analysis protocols and programming, protocols descriptions, diagnostic programs and test results, point-of-use information, analysis results data, and background information. Acquired data information can be stored as analog or digital and can be raw data, processed data or a combination of both.

System control data include synchronization data to enable the device to function at the correct angular velocity/velocities and accelerations and data relating to physical parameters of disk. Disk configuration and compatibility data include data regarding the type of disk (configuration of on-disk devices, valves, and reagent, reaction and detection chambers) used to determine the applicability of desired testing protocols; this data provides a functional identity of the type of disk and capabilities of the disk. It can be also form part of an interactive feedback system for checking platform components prior to initiation of an assay on the disk. Disk identify and serial numbers are provided encoded on each disk to enable exact identification of a disk by fabrication date, disk type and uses, which data are encoded by the manufacturer, and user information, which is written to the disk by the user. Also included in disk data is a history of procedures performed with the disk by the user. Also included in the disk data is a history of procedures performed with the disk, typically written for both machine recognition (i.e., how many and which assays remain unused or ready for use), as well as information written by the user.

Advantageous embodiments of such devices and controlling and information processing components thereof are disclosed in U.S. Ser. No. 08/768,990, filed Dec. 18, 1996, incorporated by reference.

The invention also provides platforms comprising a multiplicity of detection or cell accumulation chambers and arrays of these components in fluid communication with sample input means, reservoirs, waste receptacles and other components of the invention.

It will be recognized by those with skill in the art that such embodiments are useful for multiplex assay of a single sample or assays of multiple samples. Platforms of the invention are provided having, for example, multiple embodiments of the detection or cell accumulation chambers in fluid communication with one or a multiplicity of sample entry ports, or one or multiple embodiments of a waste receptacles in fluid communication with the detection or cell accumulation chambers of the invention. Also provided are multiplex embodiments of staining reservoirs provided in the platforms of the invention, so that multiplex staining of particulates, preferably cells, retained on the platforms of the invention, can be achieved by the sequential or simultaneous application to the detection or cell accumulation chambers of the platforms of the invention.

Methods and Uses

The present invention offers a great variety of advantageous applications and embodiments of the apparatus and methods of the invention. Certain features will be common to most embodiments, however. These features include sample collection; sample application to platform, including systems adequacy tests at the time of sample application; a variety of specific assays for detecting particulates comprising a fluid sample; detection and quantitation of said particulates; data collection, processing and analysis; data transmission and storage to memory; data output to the user (including printing and screen display); and viability, metabolic, and toxicity assays performed on the platform.

Fluid samples are collected using means appropriate for the particular sample. Blood, for example, is collected in vacuum tubes in a hospital or laboratory setting, or using a lancet for home or consumer use. Urine can be collected into a sterile container and applied to the platform using conventional liquid-transfer technology. Saliva is preferably applied to the disk diluted with a small volume of a solution of distilled water, mild detergent and sugar flavoring. This solution can be provided as a mouthwash/gargle for detecting antigens, biological secretions and microorganisms. Amniotic fluid and cerebrospinal fluid are, of necessity, collected using accepted medical techniques by qualified personnel. Cultured cells are collected using established means for in vitro passage of cells. Milk is collected simply by observing appropriate levels of care to avoid contamination.

Fluid samples are optimally loaded onto the platform at a position proximal to the center of rotation in rotatable embodiments of the invention, to provide the most extensive path across the surface of the platform, and to maximize the number, length or arrangement of fluid-handling components available to interact with the sample. Multiple samples can: be applied to the platform comprising an array of multiple sample inlet ports. Devices such as those disclosed in FIGS. 13A through 13C of co-owned and co-pending U.S. Ser. No. 08/768,990, filed Dec. 18, 1996 are advantageously used for applying the sample.

Configurations of the Fluidics Apparatus for Certain Applications

An embodiment of a device according to the invention is a portable unit no larger than a portable audio CD player-consisting of disk-drive, controllers and selectors for programmable or pre-programmed angular acceleration/deceleration profiles for a limited number of procedures. Such a device is advantageous for on-site-testing applications. For example, a fluidic sample to be tested is introduced to the disk, which is inserted into the player and the appropriate program chosen. Analysis results are stored on the disk, to be later read-out by a larger player/reader unit, and/or displayed immediately to the user. Results can also be stored as the inherent state of an indicator (positive/negative status of litmus paper in different cuvettes, for example), with no other data collection or analysis performed by the device. This data would be accessed by a larger player/reader or by other means outside the field-work environment. Information about the location, time, and other conditions of sample collection are entered through the user interface. Such embodiments are useful for particulate testing in the field, e.g., testing milk samples in a barnyard setting.

Another embodiment is a stand-alone device with active communications capabilities and greater functionality. An exemplary application for such a device is as a home blood-assay unit. This device is used by an individual placing a drop of blood on the disk, inserting the disk, and initiating the assay, preferably simply by pressing a single button. One or more cytometric procedures are then performed. Assay data is transferred to software which performs the requisite analysis, either on-disk or within the device. The device can also be permanently or temporarily attached to the home-telephone line and automatically transmit either raw or reduced data to a computer at the central location which is used to analyze the data transmitted, compare the data with accepted standards and/or previous data from the same patient, make a permanent record as part of a patient's device a confirmation of receipt of the data, perhaps the data analysis, and advice or suggested/recommended course of action (such as contacting the physician).

A desk-top peripheral/host application station constitutes a device as described above with the ability to accept instructions from and respond to a host computer over one of many advantageous data-protocols. The system is capable of acting as host or can transmit data to peripherals or other networked devices and workstations. Remote accessing of pre-programmed functions, function re-programming, and real-time control capabilities are also provided.

Yet another embodiment of this application is a centralized or bedside player/reader device with associated software located as a nurses' station in a hospital. As tests are performed on disks, the information is relayed to a physician by telephone, facsimile or pager via short-range transceiver. Patient identity can be entered at the time of sample collection by the use of bar codes and light pens attached to the device, providing the advantage of positive patient/sample identification.

The device can also be provided having the above-capabilities and functionalities and in addition having an interface with an integrated computer having high-resolution graphics, image-processing and other features. The computer provides control of the device for performing the functions described above for the peripheral system, while physical integration greatly increases data-transmission rates. Additionally, the integrated system is provided with extensive analysis software and background data-bases and information. Disk-storage cassettes of carousels are also an advantageous feature of such system. An integrated system of this type is useful in a large, analytical laboratory setting.

A self-contained, preferably battery-powered, system is useful for applications in isolated environments. Examples include devices used in remote or hostile setting, such as air, water and soil testing devices used in the Arctic for environmental purposes, or for use on the battlefield for toxic chemical detection.

Applications and Uses

The platforms and devices that make up the fluidics manipulation apparatus of the invention have a wide variety of applications, due to the flexibility of the design, wherein fluids are motivated on the platform by centripetal force that arises when the platform is rotated. What follows is a short, representative sample of the types of applications encompassed within the scope of the instant invention that is neither exhaustive or intended to be limiting of all of the embodiments of this invention.

The invention is advantageously used for detecting particulates, preferably cells, more preferably microbial cells and most preferably bacterial cells in biological fluids. A specific use for the platforms of the invention is detection of microbial, particularly bacterial contamination, of milk. In this embodiment, a platform as disclosed herein or in co-owned and co-pending U.S. Ser. No. 08/768,990, incorporated by reference, is prepared by having a surface adsorbably coated with monoclonal antibody specific to *E. coli*, with the remaining sites being blocked with bovine serum albumin (BSA). A milk sample or a plurality of milk samples are introduced onto the disk in a sample port, or more preferably an array of sample ports positioned proximal to the central rotating axis of the platform. Alternative embodiments comprise such arrays in chambers whereby fluid movement is motivated by alternative means, such as pumping mechanisms; however, centripetal force motivation is preferred. Control of fluid movement is preferably controlled by valve mechanisms as disclosed herein. The samples are introduced into a detection chamber or surface or a multiplicity thereof comprising the *E. coli* monoclonal antibody and incubated for 10 to 60 min at a temperature of 20° C., ambient temperature, 37° C. or any appropriate temperature for binding the antibody to bacterial cells. The milk fluid is then removed from the detection chamber on the platform preferably by rotating the platform and opening the necessary valves controlling egress from the chamber. The detection chamber is operatively connected to at least one effluent or waste reservoir for retaining fluid purged from the detection chamber. Non-specific binding of cells and other particulates is removed from the detection chamber by washing the chamber once or repeatedly with a buffer solution, preferably containing a salt, competitor or other agent that facilitates removal of non-specifically-bound cells. Effluent from these washing steps is voided to the waste chamber through motivation of the fluid (preferably by centripetal force) through the channel connecting the detection chamber to the waste reservoir.

Detection of specifically-bound particles, preferably microbial cells is achieved in a variety of ways as follows. Visual inspection of the reaction chamber can be used to resolve cells, by observation of the chamber by an operator, or alternatively an automated or computer-aided vision system. Optical methods, including absorbance, fluorescence, chemiluminescence, bioluminescence, and light scattering, can be automated and performed using a device adapted for this purpose, preferably a device comprising means for rotating the platform to provide fluid movement on the platform. In preferred embodiments of the apparatus of the invention suitable for detecting and quantitating individual particles, preferably cells, the optical array comprises a laser light source and detection means related to conventional CD and CD-ROM technology. In such embodiments, the laser tracks the area of each of the detection chambers on the platform, and records absorbance, transmittance, light scattering and fluorescence. Means for recording the output detected by the photodiode, an avalanche photodiode, a photocell or a photomultiplier tube comprising the detector are advantageously provided as components of the device.

In the practice of certain of these methods, stains and dyes are preferably added to the cells or fluids to enhance detection of the cells. Specific examples of such stains and dyes include vital stains, cell-specific stains, fluorescent stains such as rhodamine, specific antibodies linked to fluorescent dyes, or antibodies linked to enzymes (such as horse radish peroxidase (HRP) or alkaline phosphate (AP)) capable of catalyzing the conversion of a substrate to a specifically-detectable product, or other embodiments thereof. In the practice of these methods, the stains and dyes are applied to the cells prior to specific binding in the detection chamber, or such stains and dyes are applied to the cells in the wash solution of thereafter once the cells have been specifically-bound to the detection chamber. The platform advantageously comprises reagent reservoirs containing such stains and dyes connected to the sample port, the detection chamber, or reservoirs containing washing buffers, for the appropriate introduction to the fluid or surface comprising the cells of interest.

Each of the steps of the bacterial cell detection method disclosed herein are optimized for amount, volume and time of incubation. Specific embodiments are optimized for the platforms, devices and detection systems used, and for the particulates to be detected. For example, the invention provides means for both detecting certain bacterial cells and determining whether such cells are Gram positive or Gram negative, using the appropriate application of specific staining reagents. Cell number can be quantitated either directly, by cell counting, or in relation to the amount of a specific dye or stain retained (or in the case of enzyme-linked immunoassay, produced) in the detection chamber.

The invention also provides such cells attached to a specific surface for toxicity monitoring, such as metabolic monitoring to determine the efficacy of bioactive drugs or other treatments. Ordered arrays of such, surface are provided in certain embodiments to facilitate a complete determination of the purity and sterility of certain biological samples, and for cell cytometric and cytometry applications. Exemplary arrangements of platform components which can be used to carry out this type of screening assay are presented in FIG. 4, wherein the detection chamber is substituted with a cell accumulation chamber as described herein.

The following Examples are intended to further illustrate certain preferred embodiments of the invention and are not limiting in nature.

EXAMPLE 1
Cell Counting, Identification and Monitoring

Apparatus and methods for identifying particular cells or cell types in a biological sample are provided by the invention. A platform as described herein and in co-owned and co-pending U.S. Ser. No. 08/768,990, filed Dec. 18, 1996, incorporated by reference, is prepared by having a surface advantageously comprising a detection chamber adsorbably coated with monoclonal antibody specific to *E. coli*, the remaining sites on the surface comprising the detection chamber being blocked with bovine serum albumin (BSA). A milk sample is introduced onto the platform via a sample inlet port and brought into contact with the detection chamber comprising the surface coated with the antibody. The milk is incubated in this chamber for 30 min. The platform is then rotated to remove unwanted materials from the detection chamber and into a fluid waste receptacle with which the detection chamber is in fluid communication. An amount of a buffer appropriate for washing the chamber is then added to the surface of the chamber from a wash buffer reservoir with which the detection chamber is in fluid communication and containing a washing buffer, said buffer being motivated by centrifugal force and opening of a microvalve. In a useful embodiment, the washing buffer comprises an *E. coli*-specific monoclonal antibody covalently attached to an enzyme (such as peroxidase). This incubation is allowed to proceed for 5 min. The platform is again rotated with the opening of the appropriate microvalves to remove the washing solution from the chamber and to add a solution containing an enzymatic substrate (tetramethylbenzidine and hydrogen peroxide), maintained heretofore in a reagent reservoir with which the detection chamber is in fluid communication, preferably by a microvalve-controlled microchannel. The amount of *E. coli* bound in the reaction chamber is quantitated with regard to the amount of detected enzymatic activity, which is determined spectrophotometrically by the appearance of a light-absorbing product or the disappearance of a light-absorbing substrate.

EXAMPLE 2
Somatic Cell Counting

Figure 2:
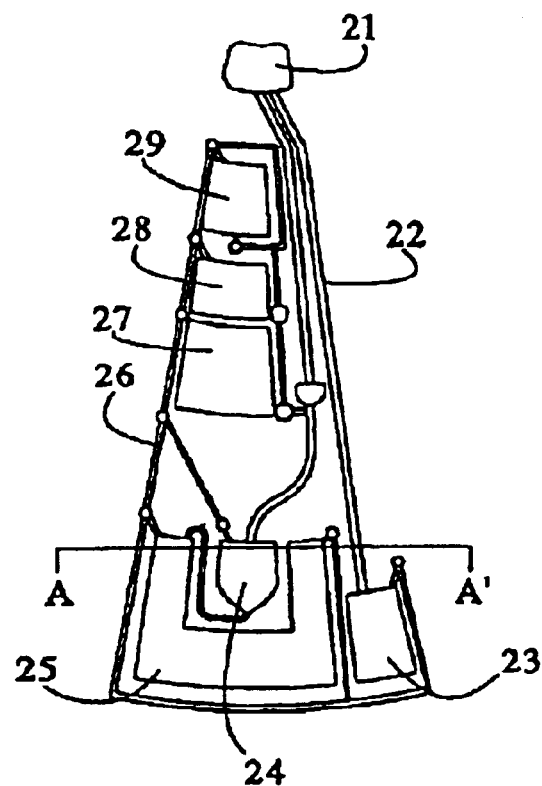
FIGS. 2 and 2A set forth an exemplar arrangement of platform components useful for enumerating particulates in a fluid, for example cell counting, and comprises a sample input port 21 connected to an overflow chamber 23 via a fluid capillary 22. The sample inlet port 21 is fluidically connected to the binding chamber 24, which is in turn connected to a waste chamber 25. Air displacement channels 26 facilitate filling of chambers. Wash buffer chambers 27 and 29, and a dye chamber 28 are fluidically connected to the binding chamber 24 via fluid capillaries 22.
Figure 2A:
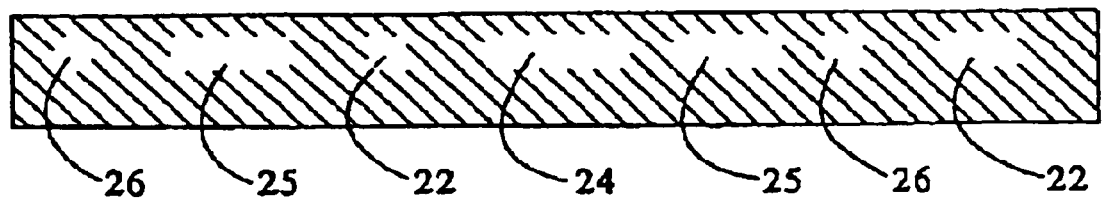
Figure 3A:
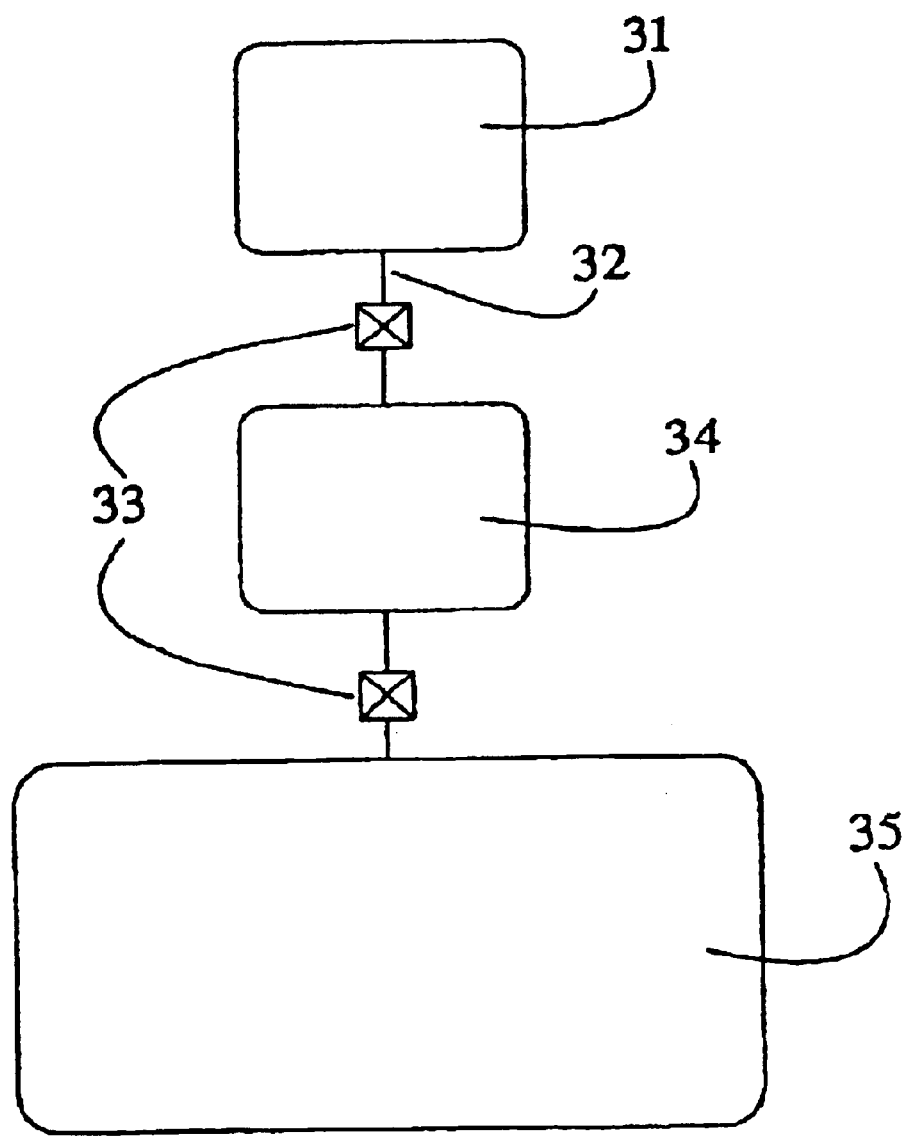
FIG. 3A comprises a wash buffer chamber 31, linked by a capillary 32 containing a valve 33 to a binding chamber 34. The binding chamber is linked to a waste chamber 35.
Figure 3B:
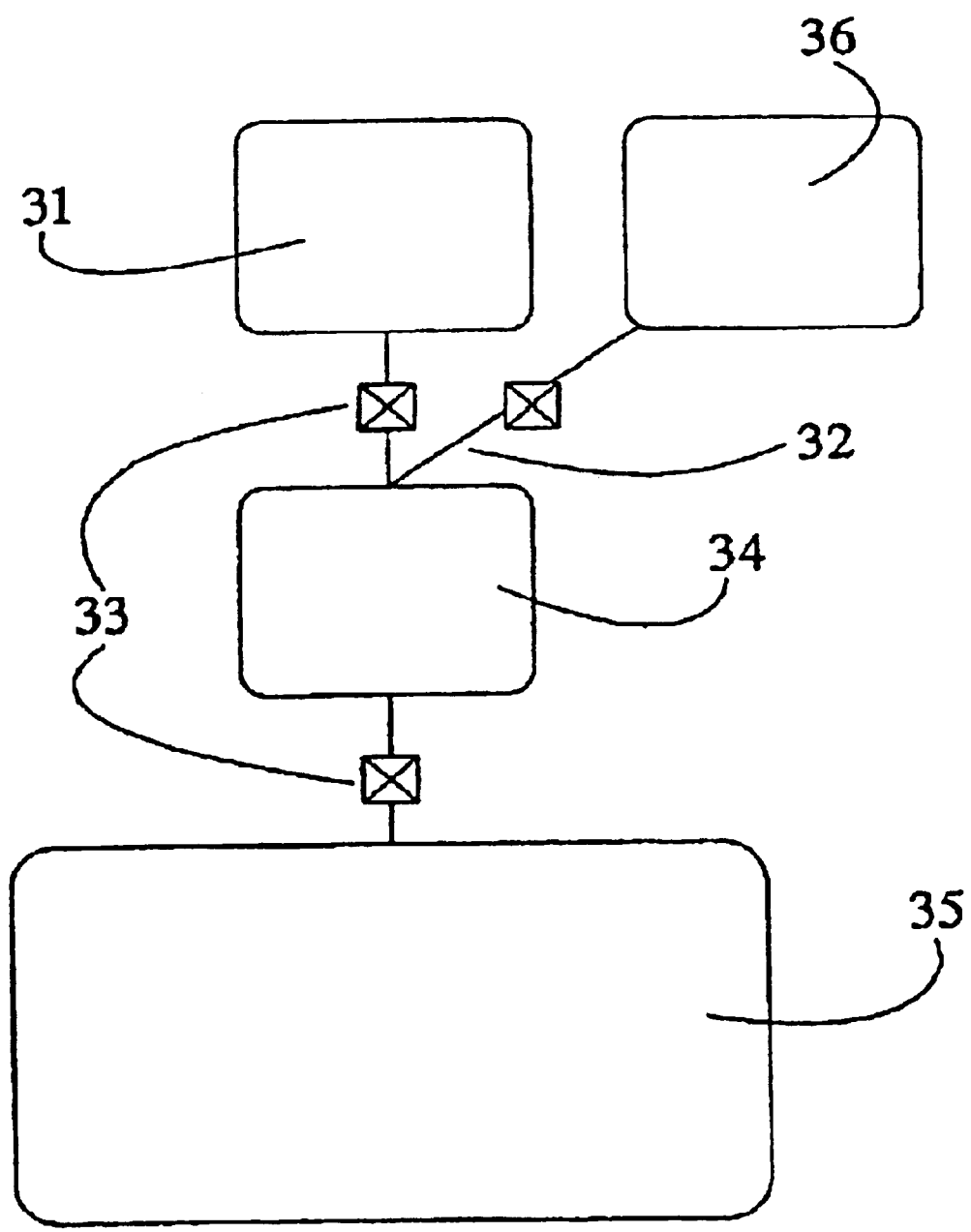
FIG. 3B incorporates a dye chamber 36 fluidically connected via a capillary 32 and valve 33 to the binding chamber 34.
Figure 3C:
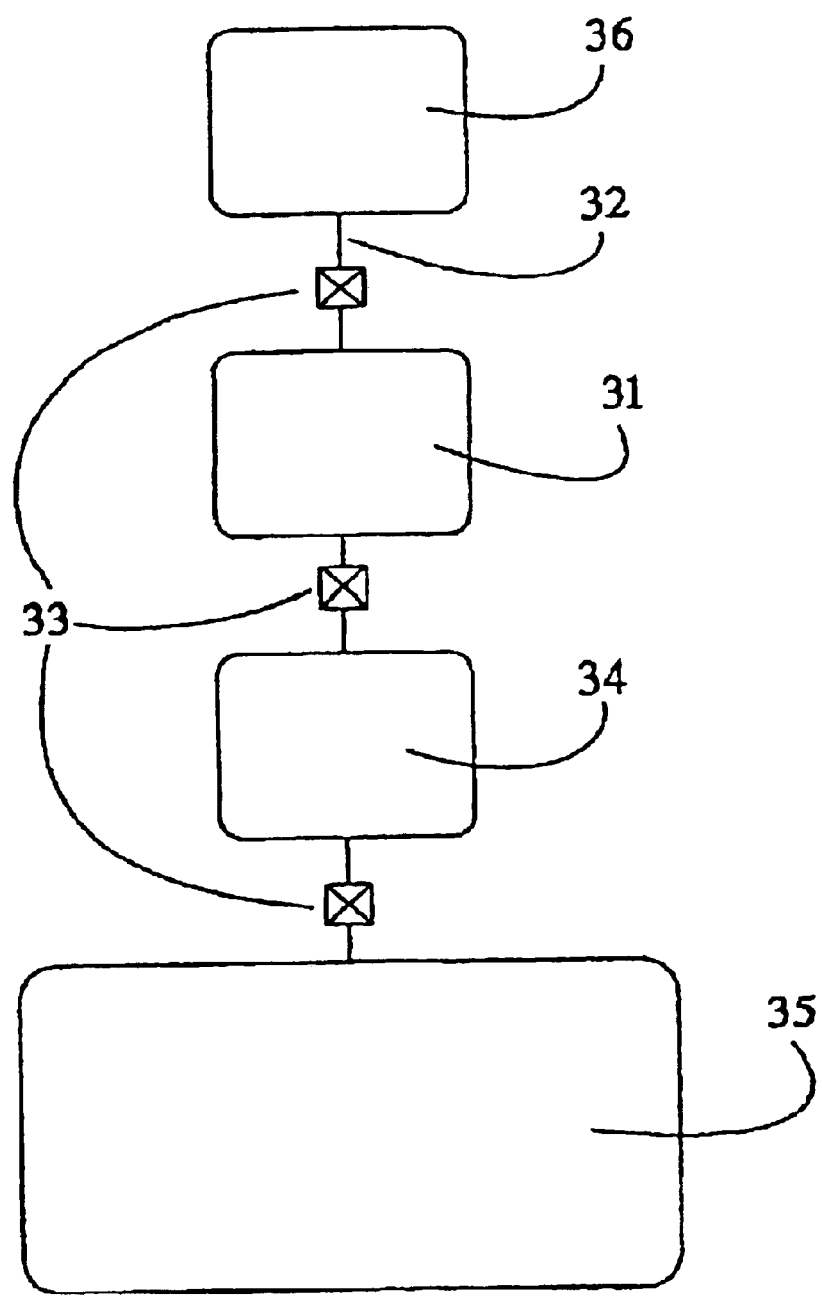
FIG. 3C provides an alternate arrangement of the components of FIG. 3B.
Figure 3D:
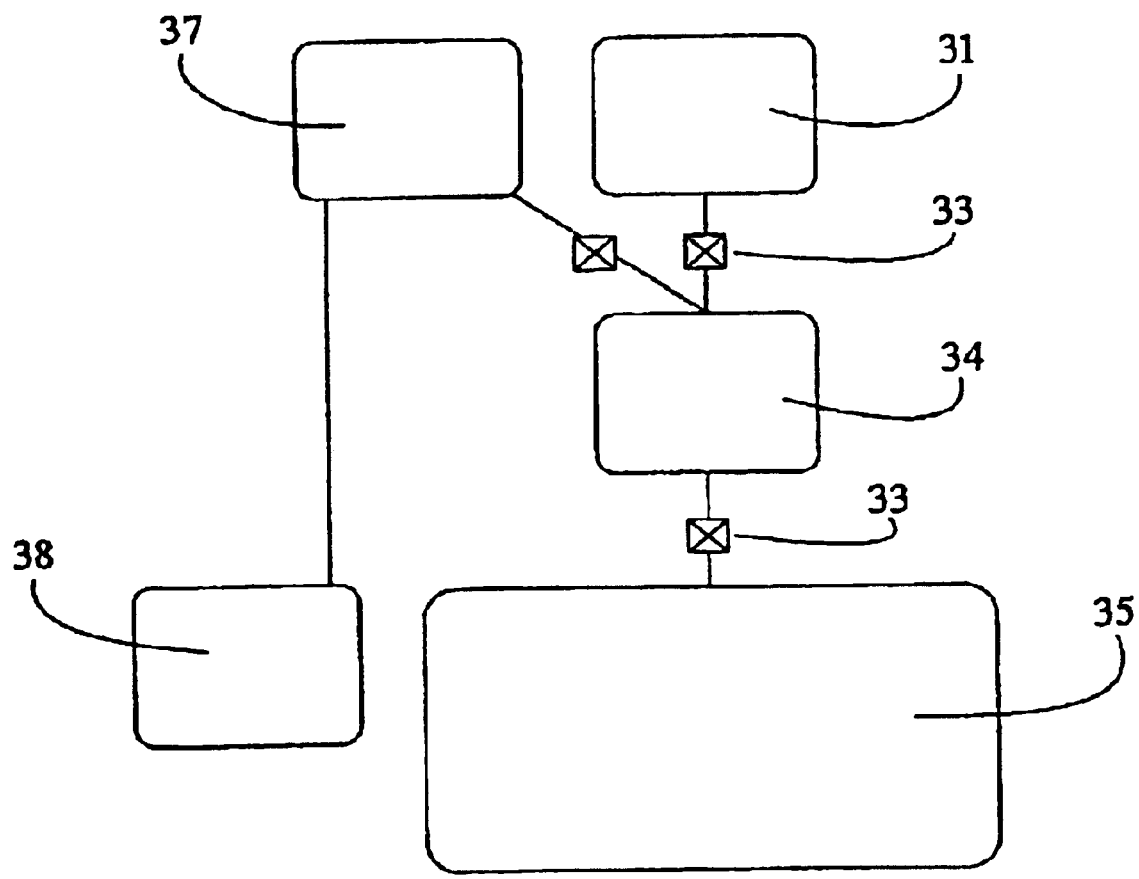
FIG. 3D adds a sample inlet port 37 and a sample overflow chamber 38 to the arrangement of components pictured in FIG. 3A.
Figure 3E:
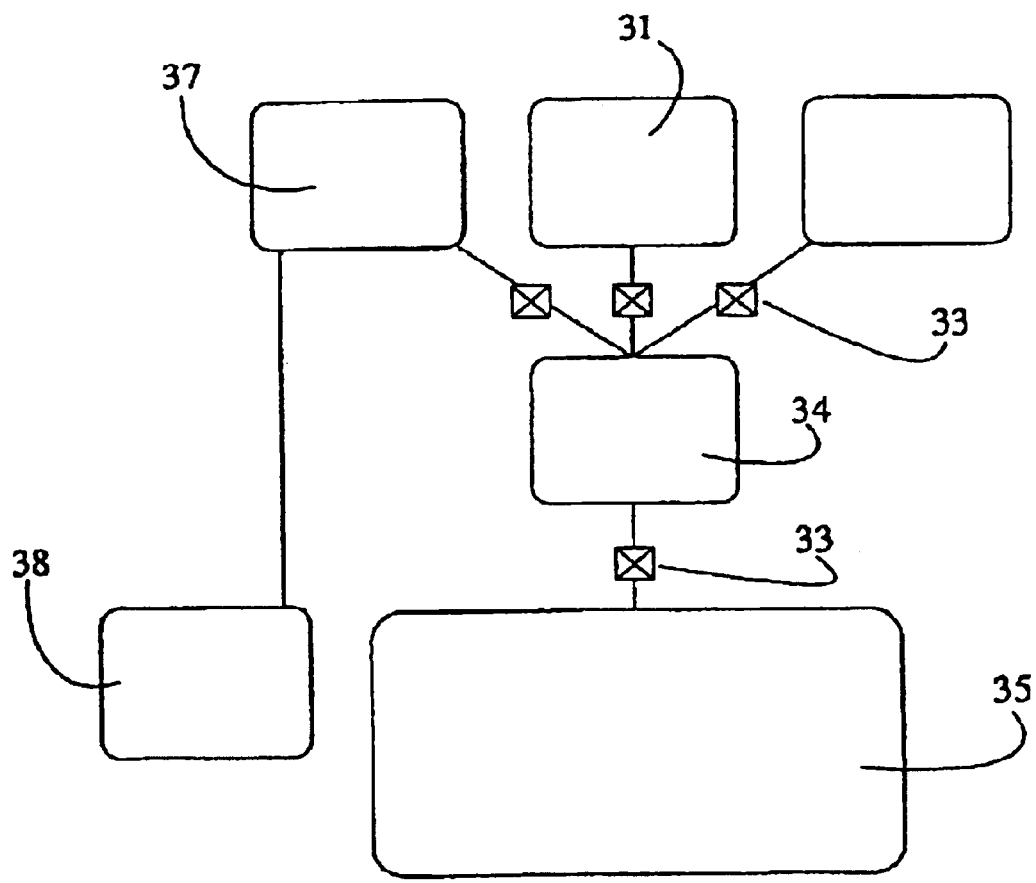
FIG. 3E adds a sample inlet port 37 and a sample overflow chamber 38 to the arrangement of components pictured in FIG. 3B.
Figure 3F:
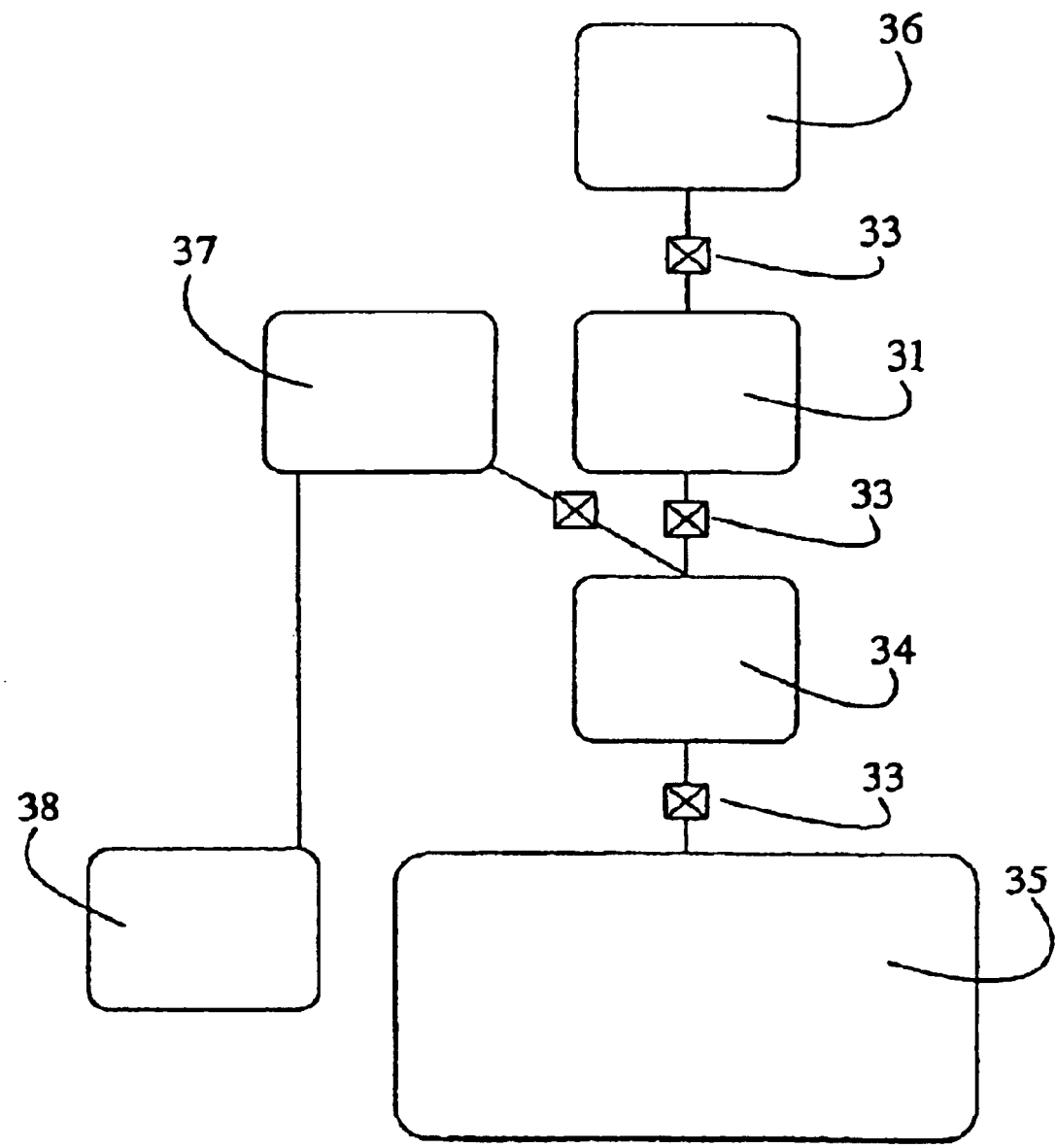
FIG. 3F adds a sample inlet port 37 and a sample overflow chamber 38 to the arrangement of components pictured in FIG. 3C.
Figure 3G:
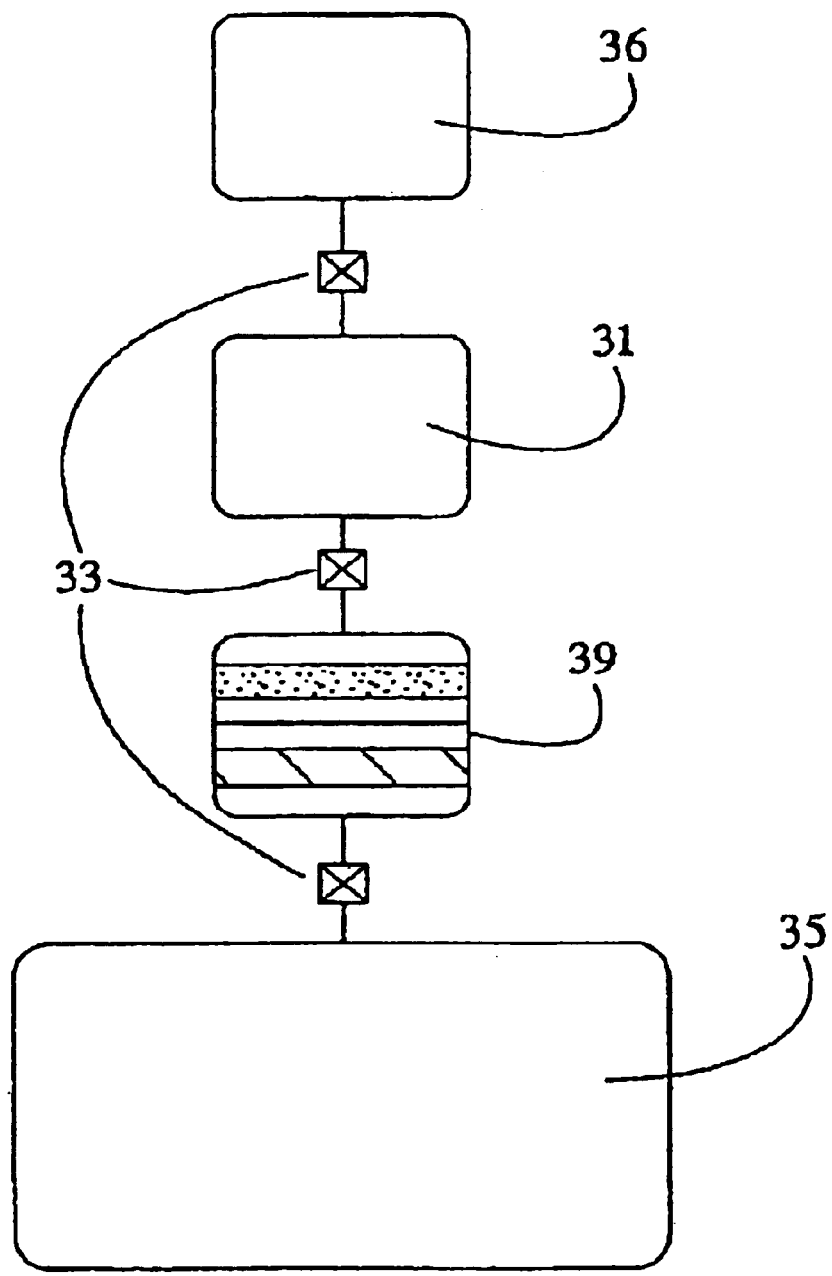
FIG. 3G is similar to FIG. 3C but incorporates a binding chamber 39 containing a number of first members of the binding pairs.
Figure 3H:
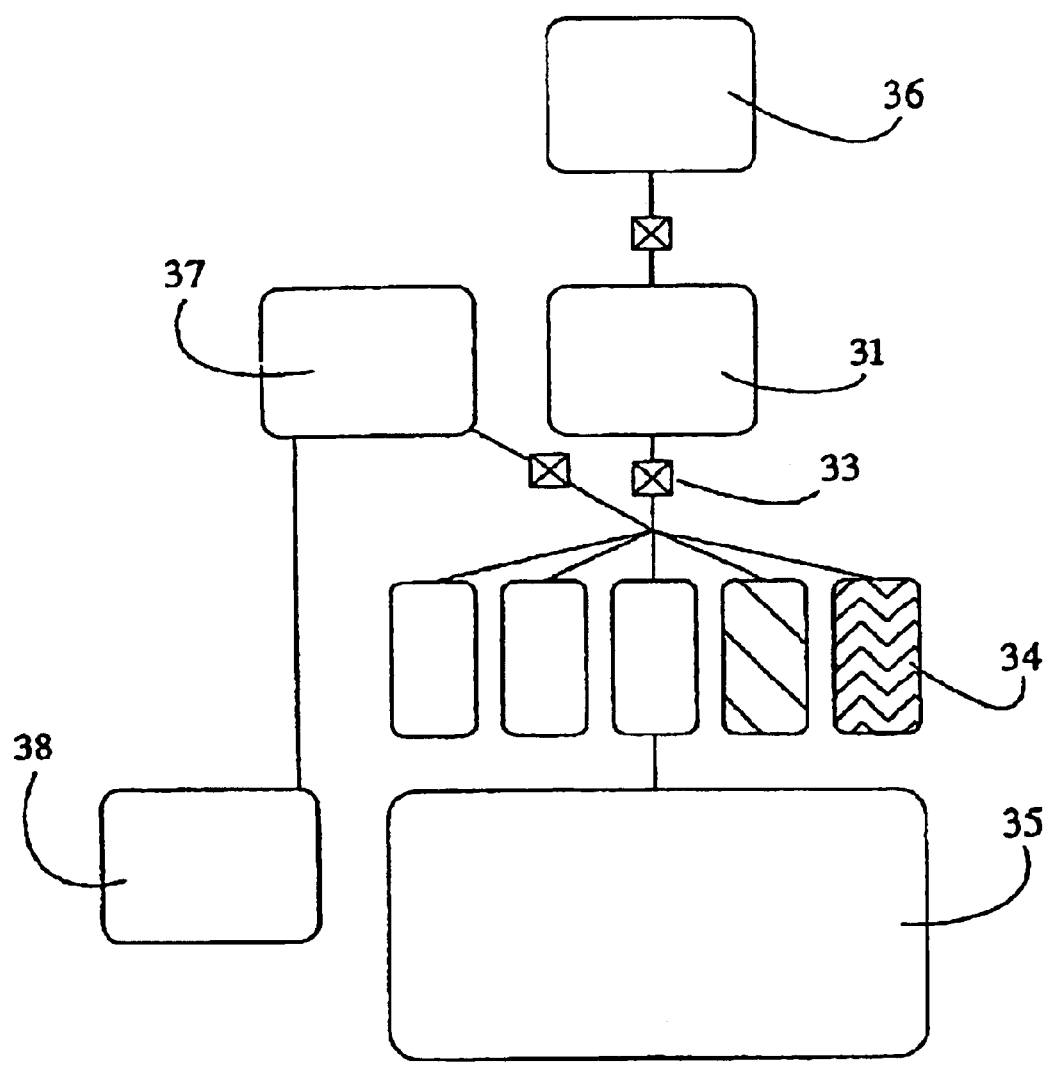
FIG. 3H is similar to 3F except that the binding chamber 34 has been replaced by a number of chambers in which distinct specific binding reagents comprising first members of an affinity binding pair have been deposited.

An example of an assay for a mammalian cell in a biological fluid is the detection of somatic cell in a sample of cow's milk. The assay system is illustrated in FIGS. 2 and 2A and consists of a sample entry port 21, wash buffer chambers 27 and 29 (containing a wash buffer solution of 25 mM potassium hydrogen (KH) phthalate, pH 5/0.001% Triton X-100), a dye chamber 28 (containing a staining solution of 0.002% ethidium bromide in KH-phthalate buffer), and a binding/detection chamber 24, which incorporates a binding surface which has been modified with a specific binding reagent comprising antibodies specific for bovine leukocyte cell surface antigens. The platform also comprises an overflow reservoir 23 and waste receptacle 25. The milk sample is introduced, optionally after pretreatment, for example, to remove fat globules or other non-specific particulates, into the sample entry port on the platform. Platforms of the invention can be provided with wash buffer and stain or can be added to the platform immediately before use. The platform is rotated at a gradually increasing rate to move the excess fluid from the sample chamber into the overflow chamber. The speed is increased further to drive the sample into the binding/detection chamber, where it contacts the surface coated with the specific binding reagent. The milk is then incubated in the chamber for 30 minutes. Following incubation, a valve connecting the wash buffer reservoir to the binding/detection chamber is opened and fluid flow achieved, e.g., by increasing the rotation rate or by actuating a thermal valve, so that the wash buffer flushes the milk sample out of the chamber and into the waste receptacle. After the wash buffer has replaced the milk in the binding/detection chamber, a valve connecting the dye chamber containing the staining solution to the binding/detection chamber is opened so that the staining solution fills the binding chamber and replaces the wash buffer. After allowing a sufficient time for the dye to stain the cells, the number of cells bound to the chamber are observed visually using source light at wavelengths between 510 and 560 nm derived by filtering the light of a mercury arc lamp, and a long pass filter to detect the emitted fluorescence.

Alternatively, in a mechanically-simpler embodiment, the milk sample is pretreated by adding buffer and dye (described in greater detail in S. Williams (ed.), 1984, *Official Methods of Analysis of the AOAC*, 14$^{th}$ ed., Assoc. of Official Analytical Chemists, Arlington, Va.) off-platform, then the sample is introduced onto the platform. The platform is rotated to transfer the sample into the binding chamber where the cells settle and bind to the specific binding reagent. A washing step is performed by increasing the rotation rate of the platform to transfer a washing fluid into the binding chamber, followed by cell staining and detection as described above.

EXAMPLE 3
Drug Discovery

Another example of the apparatus and methods of the invention is automated evaluation of the effect of test molecules on a population of cells. Advantageously, the cells are bacterial or mammalian cells, and originate from either primary cultures (i.e. freshly harvested, particularly hematopoietic cells) or established cell lines. Viability, metabolic activation (as indicated by changes in membrane potential, intracellular pH and/or intracellular free calcium concentration) and other cellular responses are assessed using the detection means of the invention described here. Test molecules include drugs such as antibiotics, compounds being assessed for cellular toxicity, or molecules being screened to activate or block a particular receptor on a cell. The platforms or disks of the invention are used generally according to the invention as follows. Cells are cultured or isolated, stained with a suitable dye, exposed to the test molecule, and the cells then analyzed by monitoring or measuring the optical properties of the cells associated with cell viability, metabolic activation or other cellular response to the test compound. The sequence in which these operations are performed is dependent on the test compound; in certain embodiments these operations are performed sequentially while in others the operations are performed simultaneously.

One example of a preferred method of toxicology testing useful with the platforms of the invention is the neutral red uptake test (A. M. Goldberg and I. M. Frazier, 1989, "Alternatives to Animals in Toxicity Testing", Sci. Amer. 261: 24–30). In this assay, cells are exposed to a cytological dye (specifically, a vital stain) and a potential toxin, and the viability of the cells detected after incubation is related directly to the amount of dye-taken up by the cells. In another application, drug discovery, cells are stained with fluorescent indicators that respond to changes in membrane potential, intracellular pH or ion concentrations, and then challenged with the test molecule. The cytological response is measured using an optical detection system which detects fluorescence. In a particular application in the field of drug discovery, high-throughput screening of potentially biologically active compounds, e.g., test molecules that activate a particular receptor on a cell of interest are contacted with cells and the binding constant of successful candidate test molecules determined by studying the dependence of test molecule concentration on cell activation. For example, in Type II, or adult-onset, diabetes, treatment consists of administering drugs which increase insulin production by stimulating the beta cells of the pancreas. One class of drug administered in this treatment is sulfonylureas, which are believed to act by blocking ATP-dependent potassium ion channels. As a consequence of sulfonylurea treatment, the cells are depolarized, leading to opening of voltage dependent calcium ion channels and increased insulin secretion. A platform arrangement useful in high throughput screening for insulin-stimulating drugs is illustrated in FIGS. 2 and 2A. The platform consists of a cell accumulation chamber 24 in which cells are cultured; a test compound buffer chamber 29 for introducing a predetermined concentration of the test compound to the cell accumulation chamber; a dye chamber containing a cytological stain solution 27; a wash buffer chamber 28; and a waste receptacle chamber 25. Rat insulinoma cells (strain RINm5F) are resuspended in culture medium (e.g. RPMI 1640 supplemented with serum, antibiotics and glucose) and introduced onto the accumulation chamber of the device. The cells are then cultured at 37° C. for a sufficient period of time to allow the cells to attach to the platform surface. Following attachment, the staining and test molecule chambers are loaded. The cells are stained with a solution of a calcium-sensitive fluorescent dye (e.g. Fluo-3) prepared in a buffered medium (e.g. HEPES-NaOH) supplemented with glucose at a dye concentration of about 1 to 10 micromolar. A solution of a test molecule (e.g. 1 mM tolbutamide) in the same buffer is added to the test molecule chamber. The assay is initiated by rotating the platform at a gradually increasing rate with opening of a valve connecting the stain to the cell accumulation chamber, and increasing the rotation rate or actuating a thermal valve, so that the stain flushes the cell culture medium out of the chamber. The staining solution is allowed to remain in the chamber for a sufficient period of time to effect staining of the cells (from minutes to an hour). Following this, the valve connecting the test molecule to the binding chamber is opened (by increasing rotation rate or actuating a thermal valve). The solution of the test molecule solution replaces the stain solution and fills the cell accumulation chamber. The effect of the test compound on the cells is assayed by determining intracellular calcium concentration by detecting fluorescence of the cells using fluorescence optics, such as a fluorescence microscope using a filtered (450–490 nm) mercury lamp as light source, and a photomultiplier tube and filter (passing wavelengths greater than 520 nm); typically, intracellular calcium concentration is initiated monitored continuously over a time course of the assay.

It will be recognized that the methods described in this example can be advantageously adapted to assays for antibiotic susceptibility of bacterial cells and toxicological testing.

It should be understood that the foregoing disclosure emphasizes certain specific embodiments of the invention and that all modifications or alternatives equivalent thereto are within the spirit and scope of the invention.

What is claimed is:

1. An apparatus for detecting a particulate in a fluid, the apparatus comprising
   a platform comprising a substrate having a surface, wherein said surface defines a detection chamber comprising an area that is coated with a specific binding reagent that specifically binds to the particulate to be detected;
   a fluid sample input means in fluid communication with the detection chamber that is coated with the specific binding reagent;
   a wash buffer reservoir containing a wash buffer in fluid communication with the detection chamber that is coated with the specific binding reagent;
   a fluid waste receptacle in fluid communication with the detection chamber that is coated with the specific binding reagent;
   wherein an amount of a fluid sample comprising a particulate is moved from the fluid sample input means to the detection chamber and incubated thereon for a time sufficient to result in specific binding between the particulate in the fluid sample and the specific binding reagent in the detection chamber; and
   wherein the fluid sample is replaced with the wash buffer and displaced into the fluid waste receptacle; and
   wherein the wash buffer is further displaced into the fluid waste receptacle; and
   wherein a particulate specifically bound to the detection chamber is specifically bound to the specific binding reagent and is detected thereupon, further comprising a device, wherein the device has a surface or cavity that accommodates the platform, and a light source positioned to illuminate the platform and wherein the detection chamber further comprises alternating transparent and reflective regions.

2. An apparatus according to claim 1, wherein the alternating transparent and reflective regions define a pattern in the detection chamber.

3. An apparatus according to claim 1 wherein the specific binding reagent is present on the surface of the platform on a transparent region thereof.

4. An apparatus for detecting a particulate in a fluid, the apparatus comprising
   a platform comprising a substrate having a surface, wherein said surface defines a detection chamber comprising an area that is coated with a specific binding reagent that specifically binds to the particulate to be detected;
   a fluid sample input means in fluid communication with the detection chamber that is coated with the specific binding reagent;

a wash buffer reservoir containing a wash buffer in fluid communication with the detection chamber that is coated with the specific binding reagent;

a fluid waste receptacle in fluid communication with the detection chamber that is coated with the specific binding reagent;

wherein an amount of a fluid sample comprising a particulate is moved from the fluid sample input means to the detection chamber and incubated thereon for a time sufficient to result in specific binding between the articulate in the fluid sample and the specific binding reagent in the detection chamber;

wherein the fluid sample is replaced with the wash buffer and displaced into the fluid waste receptacle; and wherein the wash buffer is further displaced into the fluid waste receptacle; and wherein a particulate specifically bound to the detection chamber is specifically bound to the specific binding reagent and is detected thereupon, wherein the detection chamber that is coated with a specific binding reagent is further treated with a blocking agent that prevents non-specific binding to the surface of the platform, and wherein the specific binding reagent is present in the detection chamber on transparent regions thereof, and the blocking reagent is present in the detection chamber on transparent and reflective regions thereof.

* * * * *